United States Patent
Loncar

(10) Patent No.: US 7,956,727 B2
(45) Date of Patent: Jun. 7, 2011

(54) METHODS AND SYSTEMS FOR MEDICATION MANAGEMENT

(75) Inventor: Srdjan Loncar, East Brunswick, NJ (US)

(73) Assignee: Carespeak Communications, Inc., East Brunswick, NJ (US)

( * ) Notice: Subject to any disclaimer, the term of this patent is extended or adjusted under 35 U.S.C. 154(b) by 386 days.

(21) Appl. No.: 12/054,216

(22) Filed: Mar. 24, 2008

(65) Prior Publication Data

US 2008/0238666 A1 Oct. 2, 2008

Related U.S. Application Data

(60) Provisional application No. 60/919,500, filed on Mar. 22, 2007, provisional application No. 60/925,048, filed on Apr. 18, 2007, provisional application No. 61/002,504, filed on Nov. 9, 2007.

(51) Int. Cl.
*G08B 1/00* (2006.01)

(52) U.S. Cl. ........... 340/309.16; 340/309.7; 340/539.12; 340/573.1; 368/13; 600/300; 705/3

(58) Field of Classification Search .......... 340/539.12–539.29, 309.16–309.07, 340/573.1, 309.8, 309.9; 705/2–3; 368/10, 368/13; 604/131; 600/300
See application file for complete search history.

(56) References Cited

U.S. PATENT DOCUMENTS

| | | | |
|---|---|---|---|
| 5,612,869 A | 3/1997 | Letzt et al. | |
| 5,950,630 A | 9/1999 | Portwood et al. | |
| 5,995,938 A | 11/1999 | Whaley | |
| 6,294,999 B1 | 9/2001 | Yarin et al. | |
| 6,578,003 B1 | 6/2003 | Camarda et al. | |
| 6,587,829 B1 | 7/2003 | Camarda et al. | |
| 6,771,174 B2 * | 8/2004 | Broas ..................... | 340/573.1 |
| 7,287,031 B1 | 10/2007 | Karpf et al. | |
| 2001/0025246 A1 | 9/2001 | Haines et al. | |
| 2002/0027507 A1 | 3/2002 | Yarin et al. | |
| 2002/0169635 A1 | 11/2002 | Shillingerburg | |
| 2004/0015132 A1 | 1/2004 | Brown | |
| 2005/0102159 A1 | 5/2005 | Mondshine | |
| 2005/0165626 A1 | 7/2005 | Karpf et al. | |
| 2005/0187789 A1 | 8/2005 | Hatlestad et al. | |
| 2005/0187790 A1 | 8/2005 | Lapsker | |
| 2005/0216307 A1 | 9/2005 | Clements et al. | |
| 2006/0031101 A1 | 2/2006 | Ross et al. | |
| 2006/0122866 A1 | 6/2006 | Hadl | |
| 2006/0218011 A1 | 9/2006 | Walker et al. | |
| 2007/0016443 A1 | 1/2007 | Wachman et al. | |
| 2007/0027712 A1 | 2/2007 | Lapsker | |
| 2007/0061166 A1 | 3/2007 | Ramasubramanian et al. | |
| 2007/0143138 A1 | 6/2007 | Ross et al. | |

(Continued)

*Primary Examiner* — Brent Swarthout
(74) *Attorney, Agent, or Firm* — Pepper Hamilton LLP

(57) ABSTRACT

A method of monitoring a patient's compliance with a medication regimen may include identifying a patient, identifying a medication prescribed to the patient and determining one or more intake times associated with the medication. For each intake time, an alert reminding the patient to take the medication may be generated, and the alert may be transmitted to a mobile device associated with the patient. Receipt of the alert by the mobile device may trigger one or more of an audible alarm, a visual alarm and a tactile alarm on the mobile device. If an indication of compliance is not received from the mobile device within a predefined period of time, a caregiver associated with the patient may be notified.

16 Claims, 21 Drawing Sheets

U.S. PATENT DOCUMENTS

| | | |
|---|---|---|
| 2007/0167688 A1 | 7/2007 | Ross et al. |
| 2007/0168228 A1 | 7/2007 | Lawless |
| 2007/0174092 A1 | 7/2007 | Lara et al. |
| 2007/0255600 A1 | 11/2007 | Cantor |
| 2007/0260487 A1 | 11/2007 | Bartfeld et al. |

* cited by examiner

INTAKE INFORMATION

DAYS:
    NON-DAILY:
        MON   TUE   WED   THUR   FRI   SAT

UNITS PER INTAKE:  1
TIMES PER DAY:  1

ALARM TIMES:   HOUR  MINUTES  AM/PM
    TIME # 1:   10     15     AM

FIG. 3

|   |   | 420 | 425 |
|---|---|---|---|
|   |   | PHYSICIAN | PHARMACY |
|   |   | DR. SMITH | RITE AID |
|   |   | (212) 323-9564 | (212) 214-8958 |

| NO. | MEDICATION | COMPLIANCE* | REFILL | SCHEDULE | IMAGE | EDIT |
|---|---|---|---|---|---|---|
| 405—1 | CEFUROXIME 500 mg | 100% | NO | 1 PILL  2 PER DAY   I TAKE WITH FOOD<br>8:30 AM EVERY DAY |  | EDIT<br>REMOVE |
| 405—2 | MOTRIN 200 mg | 100% | NO | 410— 4 PILL I 1 PER DAY<br>415— 8:00 PM ON SUN | ○ | EDIT<br>REMOVE |
| 405—3 | GLUCOSAMINE 1200 mg | 100% | NO | 1 PILL I 2 PER DAY   I   TAKE WITH PLENTY<br>9:00 AM, 7:00PM EVERY DAY   OF WATER |  | EDIT<br>REMOVE |
| 405—4 | FISH OIL 1200 mg | 100% | NO | 1 PILL I 2 PER DAY<br>400  9:00 AM, 7:00PM EVERY DAY |  | EDIT<br>REMOVE |

FIG. 4

CREATE REFILL ALERTS

REFILL ALERT          600 — ☐ (CHECK BOX TO RECEIVE REFILL REMINDER)

NUMBER OF UNITS IN CONTAINER:     601 — 50
(e.g. PILLS, VIALS, etc.)

HOW MANY DAYS IN ADVANCE DO YOU WANT TO RECEIVE REFILL ALERT?    602 — 3

DO YOU WANT REFILL REQUEST AUTOMATICALLY SENT TO PHARMACY?    603 — ◉ YES ○ NO

605 — ZIP CODE
02154

CHOOSE PHARMACY: — 604
◉ CVS
○ DUANE READ
○ RITE AID
○ OTHER

YOU WILL RECEIVE SMS MESSAGE WHEN REFILL ORDER HAS BEEN PLACED WITH PHARMACY OF YOUR CHOICE

SEND ME SMS NOTICE WHEN PRESCRIPTION IS READY TO BE PICKED UP?    606 — ☐ (CHECK HERE)

SAVE — 607

FIG. 6

CEFUROXIME 500 mg

INTAKE INFORMATION
___

DAYS: DAILY ▶ — 800

UNITS PER INTAKE: 1 ▶ — 810

TIMES PER DAY: 1 ▶ — 805

815 — ALARM TIMES:

|  | HOUR | MINUTES | AM/PM |
|---|---|---|---|
| TIME #1: | 8 ▶ | 30 ▶ | AM ▶ |

CREATE REFILL ALERT
___

REFILL ALERT: — 820  ☑ (CHECK BOX TO RECEIVE REFILL REMINDER)

NUMBER OF UNITS IN CONTAINER — 825   50
(e.g. PILLS, VIALS, etc.):

HOW MANY DAYS ADVANCE NOTICE   3
SHOULD YOU GET YOUR REFILL ALERT?

ADDITIONAL INFORMATION — 830
___

PRESCRIBING PHYSICIAN: — 835   DR. JOE KLEIN
                      840 — 2122343211   (10 DIGITS, NO SPACES, OR DASHES)

DISPENSING PHARMACY: — 845   RITE AID
                    850 — 2123423221   (10 DIGITS, NO SPACES, OR DASHES)

FIG. 8

PAUL, TIME TO MEASURE
GLUCOSE LEVEL

FIG. 10A

PAUL'S READING IS
OUT OF RANGE!

GLUCOSE: 150
ACCEPTABLE RANGE : 80-130

FIG. 10B

HERE ARE PAUL'S
REPORTED VALUES :

GLUCOSE : 120

FIG. 10C

PAUL DID NOT REPORT 9 AM
SCHEDULED READING.
PLEASE CALL PAUL AT
555-111-1000

FIG. 10D

| DATA | GLUCOSE READING (mg/dl) | | | |
|---|---|---|---|---|
| | 9AM | 1PM | 6PM | 9PM |
| 3/1/2007 | 124 | 132 | 134 | 123 |
| 3/2/2007 | 134 | 135 | 144 | 126 |
| 3/3/2007 | 130 | 131 | 140 | 122 |
| 3/4/2007 | 126 | 127 | 143 | 125 |
| 3/5/2007 | 124 | 132 | 134 | 123 |
| 3/6/2007 | 127 | 135 | 137 | 126 |
| 3/7/2007 | 123 | 131 | 133 | 122 |
| 3/8/2007 | 116 | 141 | 136 | 125 |
| 3/9/2007 | 124 | 134 | 134 | 123 |
| 3/10/2007 | 127 | 137 | 127 | 126 |
| 3/11/2007 | 123 | 133 | 137 | 119 |
| 3/12/2007 | 133 | 129 | 130 | 122 |
| 3/13/2007 | 124 | 132 | 134 | 123 |
| 3/14/2007 | 127 | 135 | 137 | 126 |
| 3/15/2007 | 123 | 145 | 137 | 122 |
| 3/16/2007 | 114 | 138 | 133 | 125 |
| 3/17/2007 | 105 | 132 | 136 | 123 |
| 3/18/2007 | 108 | 125 | 129 | 126 |
| 3/19/2007 | 118 | 116 | 132 | 122 |
| 3/20/2007 | 114 | 112 | 128 | 125 |
| 3/21/2007 | 124 | 132 | 138 | 123 |
| 3/22/2007 | 127 | 135 | 129 | 133 |
| 3/23/2007 | 123 | 145 | 132 | 129 |
| 3/24/2007 | 119 | 136 | 128 | 139 |
| 3/25/2007 | 129 | 132 | 131 | 123 |
| 3/26/2007 | 132 | 135 | 144 | 126 |
| 3/27/2007 | 128 | 126 | 140 | 122 |
| 3/28/2007 | 124 | 136 | 131 | 132 |
| 3/29/2007 | 124 | 132 | 134 | 123 |
| 3/30/2007 | 127 | 135 | 137 | 114 |
| 3/31/2007 | 123 | 131 | 133 | 110 |

MEDICATION    FISH OIL 1000 mg ⟵ 1305

DOSAGE    2 PER DAY

1325 ⟵ DATE RANGE (ENTER DATE RANGE MONTH/DATE/YEAR)

FROM:    3/15/2007
TO:    3/22/2007

WEEKLY COMPLIANCE REPORT FOR THE WEEK OF 3/15/07

| TIME | MON | TUES | WED | THR | FRI | SAT | SUN |
|---|---|---|---|---|---|---|---|
| 8:00 AM | 1 | 1 | 1 | 1 | 1 | 1 | 1 |
| 8:00 PM | 1 | 1 | 1 | 1 | 0 | 1 | 1 |

1300

1315 ⟵ GOAL    14
1310 ⟵ TAKEN    13
1320 ⟵ COMPLIANCE    93%

FIG. 13

MOTIVATIONAL PANEL

SELECT PROGRAM: LIVER TRANSPLANT ▸

SELECT MEDICATION: RAPAMUNE ▸

COMPLIANCE RATE
1400 — FROM         TO — 1405
       0% ▸         0% ▸
       0% ▸         0% ▸
       0% ▸         0% ▸

1430          MOTIVATIONAL MESSAGE                              1435
       TYPE MESSAGE HERE (MAXIMUM 150 CHARACTERS INCLUDING SPACES)    TYPE HERE SIGNATURE
                                                                     (MAX 10 CHARACTERS)
       TYPE MESSAGE HERE (MAXIMUM 150 CHARACTERS INCLUDING SPACES)    TYPE HERE SIGNATURE
                                                                     (MAX 10 CHARACTERS)
       TYPE MESSAGE HERE (MAXIMUM 150 CHARACTERS INCLUDING SPACES)    TYPE HERE SIGNATURE
                                                                     (MAX 10 CHARACTERS)

MONTH   DAY   YEAR                    MONTH   DAY   YEAR
1410 — START DATE:  3 ▸   1 ▸  2008 ▸    1415 — END DATE  4 ▸   1 ▸  2008 ▸
              HOUR   MINUTES  AM/PM             ☐ NO END DATE
1420 — DELIVERY
       TIME:        9 ▸   00 ▸    AM ▸
       DELIVERY
       FREQUENCY:  DAILY ▸ — 1425
                   MON ☐   TUE ☐   WED ☐   TH ☐   FRI ☑   SAT ☐   SUN ☐

SAVE  RESET

FIG. 14

[HOME]
LIVER TRANSPLANT
ADMINISTRATOR: JANE DOE | ☎(212) 123-4567 ⟳ | JDOE@HOSPITAL.ORG | [EDIT]
ADD PATIENT | TO SORT CLICK ON UP ⇧ OR DOWN ⇩ BUTTON

| NO. ⇧⇩ | PATIENT ⇧⇩ | COMPLIANCE ⇧⇩ | PILLS LEFT ⇧⇩ | SCHEDULE ⇧⇩ | SMS ENROLLED ⇧⇩ | MOTIVATE ON OFF | STATUS ⇧⇩ |
|---|---|---|---|---|---|---|---|
| 1. | JOSE RODRIGUEZ CELLCEPT 500mg | 93% | 15 | 8:00 AM | 8:00PM | ☐ 9/1/07 | ○ ON ○ OFF | ACTIVE |
|  | IMURAN 50mg | 89% | 20 | 8:00 AM | ☐ 9/1/07 | ○ ON ○ OFF | ACTIVE |
| 2. | ASHLEY BLACK CELLCEPT 500mg | 100% | 12 | 9:00 AM | 7:00PM | ☐ 9/3/07 | ○ ON ○ OFF | ACTIVE |
| 3. | TOM MAINLY CELLCEPT 500mg | 100% | 14 | 7:00 AM | 7:00PM | ☐ 9/1/07 | ○ ON ○ OFF | ACTIVE |
| 4. | RICHARD GOOSE CELLCEPT 500mg | 86% | 16 | 7:00 AM | 7:00PM | ☐ 9/1/07 | ○ ON ○ OFF | ACTIVE |
| 5. | ROBERT KLEIN CELLCEPT 500mg | 67% | 8 | 8:00 AM | 6:00PM | ☑ 9/3/07 | ○ ON ○ OFF | ACTIVE |
| 6. | ASHLEY JONES CELLCEPT 500mg | 100% | 12 | 8:45 AM | 8:00PM | ☐ 9/3/07 | ○ ON ○ OFF | ACTIVE |
| 7. | MARK PRICE CELLCEPT 500mg | 100% | 14 | 8:00 AM | 8:00PM | ☐ 9/1/07 | ○ ON ○ OFF | ACTIVE |
| 8. | JOSEPH BAROS CELLCEPT 500mg | 100% | 12 | 9:00 AM | 9:00PM | ☐ 9/3/07 | ○ ON ○ OFF | ACTIVE |
| 9. | THOMAS ALIENDE CELLCEPT 500mg | 93% | 13 | 8:30 AM | 7:00PM | ☐ 9/1/07 | ○ ON ○ OFF | ACTIVE |
| 10. | RICHARD GOOSE CELLCEPT 500mg | 86% | 12 | 9:00 AM | 7:00PM | ☐ 9/1/07 | ● ON ○ OFF | ACTIVE |

[ADD PATIENT]
SEND CUSTOM MESSAGE (PLEASE SELECT MESSAGE RECIPIENTS ABOVE BY SELECTING THE CHECKBOX IN THE MESSAGE COLUMN)
[TYPE MESSAGE HERE (MAX 150 CHARACTERS)]

[SEND SMS]

BACK TO TOP

FIG. 17

ADMINISTRATOR SETTINGS

1800 — PROGRAM INFORMATION

PROGRAM NAME:  HEPATITIS C  (BEST USE NAME OF CONDITION TREATED)

1805 — PROGRAM MANAGER

TIME ZONE:  EST(-5) ▸
FIRST NAME:  JOE
LAST NAME:  SMITH
CELL PHONE NUMBER:  2124569807  (10 DIGITS)
CARRIER:  ATT ▸
USER NAME:  JSMITH@MTSINAI.ORG  (MUST BE OFFICIAL E-MAIL ADDRESS)
NEW PASSWORD:  _____
RE-ENTER PASSWORD:
[SAVE]

1810 — MANAGE ACCESS PERMISSION

| NAME | PERMISSION | TIME ZONE | NUMBER | CARRIER | E-MAIL ADDRESS | STATUS (ON/OFF) |
|---|---|---|---|---|---|---|
| 1815 — JOE SMITH | ADMINISTRATOR | ▸ EST(-5) | ▸ 2124569807 | ATT | ▸ JSMITH@HOSPITAL.ORG | ✓ |
| ANITA BELL | ADMINISTRATOR | ▸ EST(-5) | ▸ 2124566470 | T-MOBILE | ▸ ABELL@HOSPITAL.ORG | ✓ |
| 1820 — MARY JONES | VIEW ONLY | ▸ EST(-5) | ▸ 2124563425 | ATT | ▸ MJONES@HOSPITAL.ORG | |

[SAVE]

ADD NEW USER

FIRST NAME, LAST NAME  CHOOSE ONE ▸ CHOOSE ONE ▸ 10 DIGITS  CHOOSE ONE ▸ ENTER E-MAIL
[ADD]

FIG. 18

1900
/ JOSE RODRIGUEZ   ACCOUNT STATUS: ON ○OFF
PATIENT ACCOUNT & CAREGIVER INFORMATION: CELL PHONE: (212) 123-4546 |EMAIL: JOSE3456@AOL.COM |
MOTHER (212) 123-4567 |FATHER (212) 123-3457 | [EDIT]
MEDICATION & TREATMENT INFORMATION ——1905

| MEDICATION | COMPLIANCE | DOSAGE | PILL COUNT | |
|---|---|---|---|---|
| 1 CELLCEPT 500mg | 78% | 1 PILL 2 TIME PER DAY | 30 | [EDIT] [DELETE] |
| 1 IMURAN 50mg | 82% | 1 PILL 1 TIME PER DAY | 30 | [EDIT] [DELETE] |

[ADD MEDICATION]

NOTES —1920
   PLEASE TYPE IN HERE ANY NOTES YOU MIGHT HAVE ABOUT PATIENT.

[ADD NOTE]

| DATE I TIME | NOTE | AUTHOR |
|---|---|---|
| 9/14/07 I 3:00PM | PATIENT COMPLIANCE RATE STRONG AT 93% AFTER 2 WEEKS. | SC |
| 9/1/07 I 9:13AM | PATIENT HAS NOT STARTED TAKING MEDICATION. PATIENT AND PARENT HAVE BEEN NOTIFIED TO START TAKING MEDICATION VIA SMS | SC |

SEND CUSTOM MESSAGE —1910
   TYPE MESSAGE HERE (MAX 160 CHARACTERS)

[SEND SMS]
MESSAGE HISTORY

| DATE I TIME | MESSAGE |
|---|---|
| 9/14/07 I 3:00PM | PLEASE CALL (212) 333-4444 TO CONFIRM TOMORROW'S APPOINTMENT |
| 9/1/07 I 9:03AM | PLEASE START USING YOUR MEDICATION RIGHT AWAY |

PATIENT ACTIVITY LOG —1915

| DATE I TIME | MESSAGE |
|---|---|
| 9/14/07 I 3:32PM | PATIENT CHANGED CELL PHONE NUMBER. |
| 9/1/07 I 11:33AM | DR. MILOH CHANGED DOSAGE FROM X TO Y |
| | |

[E-MAIL THIS PAGE] [PRINT THIS PAGE]

FIG. 19

METHODS AND SYSTEMS FOR MEDICATION MANAGEMENT

CROSS REFERENCE TO RELATED APPLICATIONS

This application claims priority to U.S. Provisional Application No. 60/919,500 filed on Mar. 22, 2007, U.S. Provisional Application No. 60/925,048 filed on Apr. 18, 2007 and U.S. Provisional Application No. 61/002,504 filed Nov. 9, 2007, each of which is incorporated by reference herein in its entirety.
Not Applicable

BACKGROUND

Non-compliance with health regimens is a serious issue facing patients and the healthcare industry. Often, a patient's treatment is affected when the patient forgets to comply with a health regimen. For example, treatment of a patient's illness may be impacted when the patient forgets to take a prescribed medication.

One of the leading problems facing patients with chronic health issues is compliance with their treatment, which consists predominantly of daily, yet often complex medication regimens. This often results in a patient's failure to take or refill medication, the taking of medication at incorrect time intervals and/or the taking of medication in incorrect dosages. While some non-compliance issues can be caused by a patient's unwillingness to comply, there are many patients who desire to comply with a health regimen, but either forget or become confused.

SUMMARY

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a," "an," and "the" include plural reference unless the context clearly dictates otherwise. Thus, for example, reference to a "patient" is a reference to one or more patients and equivalents thereof known to those skilled in the art, and so forth. Unless defined otherwise, all technical and scientific terms used herein have the same meanings as commonly understood by one of ordinary skill in the art. As used herein, the term "comprising" means "including, but not limited to."

In an embodiment, a method of monitoring a patient's compliance with a medication regimen may include identifying a patient, identifying a medication prescribed to the patient and determining one or more intake times associated with the medication. For each intake time, an alert reminding the patient to take the medication may be generated, and the alert may be transmitted to a mobile device associated with the patient. Receipt of the alert by the mobile device may trigger one or more of an audible alarm, a visual alarm and a tactile alarm on the mobile device. If an indication of compliance is not received from the mobile device within a predefined period of time, a caregiver associated with the patient may be notified.

A method of verifying compliance with a health regimen may include identifying a patient, identifying an action to be performed by the patient, identifying a time at which the action is to be performed and sending an alert to a mobile device associated with the patient at the identified time. The alert may be configured to instruct the patient to perform the action. The method may also include receiving, from the mobile device, within a predefined period of time, a measurement associated with the action, and if the measurement is not within a predefined range, notifying one or more of the patient and a caregiver.

In an embodiment, a method of locating one or more members registered with a health manager may include maintaining, by a computing device, a database comprising a plurality of members registered with a health manager and receiving, by a computing device, a search query comprising one or more search criteria. The search criteria may include one or more of a name, a diagnosis, an illness, address information, and a geographic region. For each member in the plurality of members, the one or more search criteria may be compared to a profile associated with the member. The profile may include one or more of a name associated with the member, a diagnosis associated with the member, an illness associated with the member, address information associated with the member, and a geographic region associated with the member. It may be determined whether the member satisfies the search query based on the associated profile, and if so, the member may be identified as a match. The profile of each identified member may be displayed to a user.

In an embodiment, a method of confirming compliance with a medication alert may include receiving, by a mobile device, an alert to take a medication. The alert may be received at an intake time associated with the medication. In response to receiving the alert, one or more of an audible alarm, a visual alarm and a tactile alarm may be triggered on the mobile device, and information associated with the alert may be displayed to a patient on a display screen of the mobile device. The mobile device may receive confirmation of compliance and may transmit the confirmation of compliance to a computing device.

In an embodiment, a method of verifying compliance with a health regimen may include receiving, by a mobile device at an intake time, an alert reminding a patient to perform an action associated with a health regimen, and receiving, by the mobile device, a measurement associated with the action. The measurement may be provided by the patient. The measurement may be transmitted to a computing device within a predefined period of time, and a notification may be displayed to the patient if the measurement is outside a predefined range.

BRIEF DESCRIPTION OF THE DRAWINGS

Aspects, features, benefits and advantages of the present invention will be apparent with regard to the following description and accompanying drawings, of which:

FIG. 3 illustrates an exemplary form a member may use to identify alerts to be received according to an embodiment.

FIG. 4 illustrates an exemplary medication schedule according to an embodiment.

FIG. 6 illustrates an exemplary form a patient may complete on the health manager to receive a refill reminder for a medication according to an embodiment.

FIG. 8 illustrates a screen shot of an exemplary form that a patient may use to edit one or more medications according to an embodiment.

FIG. 10A illustrates an exemplary alert that a patient may receive on a mobile device according to an embodiment.

FIG. 10B illustrates an exemplary alert that may be sent according to an embodiment.

FIG. 10C illustrates an exemplary alert that a patient and/or one or more caregivers may receive on a mobile device according to an embodiment.

FIG. 10D illustrates an exemplary message that a caregiver may receive according to an embodiment.

FIG. 13 illustrates an exemplary compliance report that may be sent to or accessed by a member according to an embodiment.

FIG. 14 illustrates an exemplary online form a member may use to create one or more motivational messages according to an embodiment.

FIG. 17 illustrates exemplary information that may be displayed to a healthcare professional regarding a plurality of patients in a program according to an embodiment.

FIG. 18 illustrates an exemplary form a healthcare professional may use to identify one or more administrator settings according to an embodiment.

FIG. 19 illustrates an exemplary form a healthcare professional may use to enter patient information according to an embodiment.

DETAILED DESCRIPTION

Figure 1:
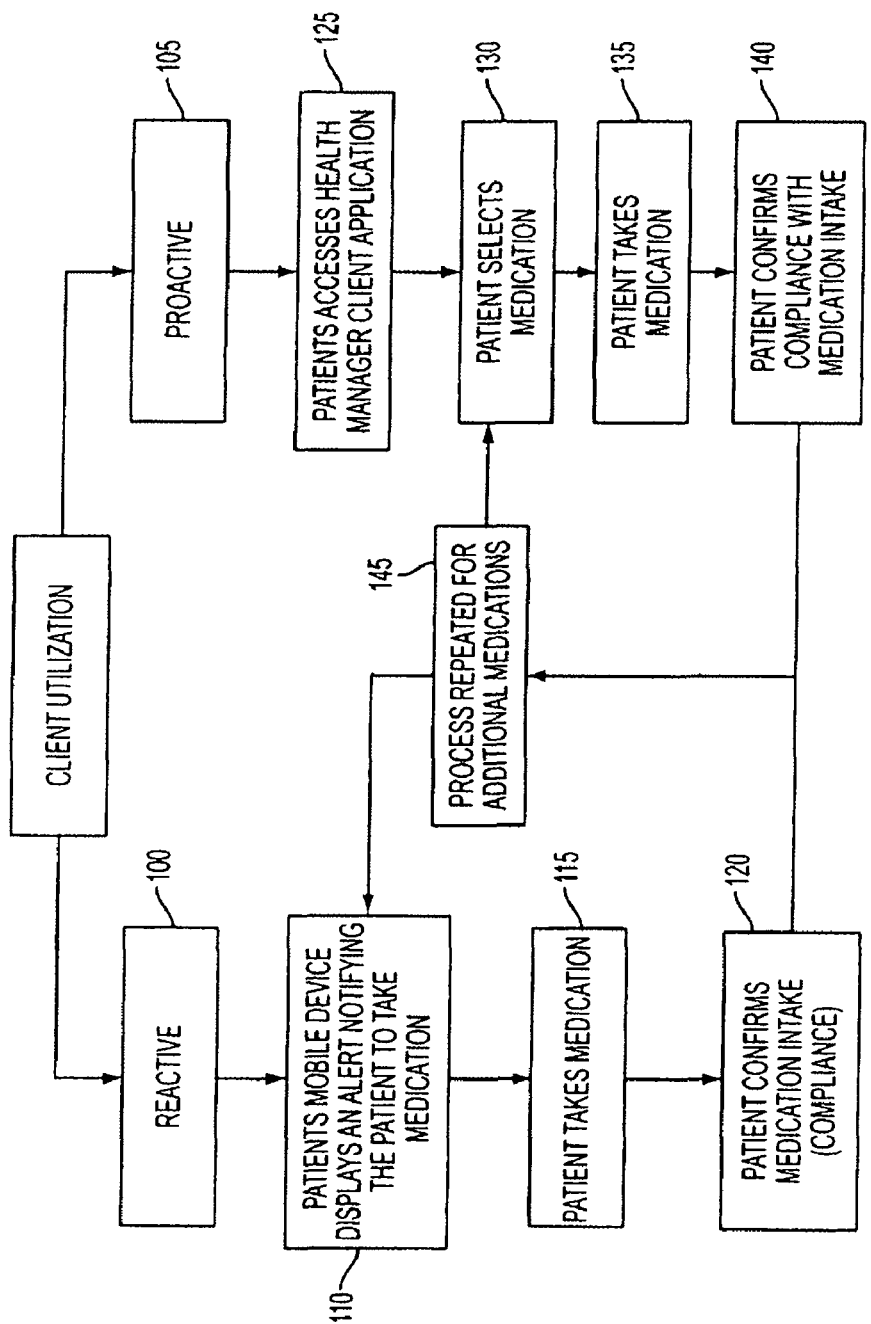
FIG. 1 illustrates an exemplary flow chart depicting reactive and proactive client utilizations according to an embodiment.

For purposes of the discussion below, a "health manager" is a software application that manages the administration of and compliance with health regimens for a plurality of patients.

A "health regimen" is a regulated plan designed to improve the health of a patient. A health regimen may include one or more actions, such as taking medication, exercising, performing physical therapy and/or the like.

A "caregiver" is a person other than the patient who has an interest in the patient's health. For example, a caregiver may be a healthcare provider, a parent, a child, a nurse, or the like.

A "mobile device" is a portable electronic device such as a cellular phone, a PDA, a media player or the like. A mobile device may have a processor and a processor-readable storage medium in communication with the processor, and may communicate with a health manager via a wireless network, a cellular telephone network and/or the like. A mobile device may have one or more of a display screen, a keypad and a touch screen.

A "member" is a subscriber to a health manager and may include a patient, a healthcare professional, a caregiver and/or the like.

"Short Message Service" ("SMS") is a communication protocol that facilitates the exchange of text messages between mobile devices.

An "MMS message" is a Multimedia Messaging Service message that may include multimedia objects such as images, audio, video and/or the like.

A "text message" is a short message, usually around 160 characters or fewer, that is sent from and/or receive by a mobile device using SMS. For purposes of the discussion below, the terms "SMS message" and "text message" are used interchangeably.

A "short code" is a special telephone number that is significantly shorter than typical telephone numbers. A short code may be used to address SMS and MMS messages from mobile devices.

A "binary SMS message" is a short message that includes binary content.

In an embodiment, a health manager may be a software application that manages the administration of and compliance with health regimens for a plurality of patients. The health manager may reside on a server or other computing device. A member may access the health manager using an Internet-enabled device such as a personal computer, a PDA, a cellular phone and/or the like.

In an embodiment, a member may select a service type associated with the health manager. A service type may correspond to how a client, such as a mobile device, may receive and transmit information. In an embodiment, a service type may include a one-way SMS, a two-way SMS or a client software application. In an embodiment, if a member selects a one-way SMS service type, the member may receive messages regarding the patient's health regimen from the health manager, but data exchange between the member's mobile device and the health manager may not occur. For example, a patient may not be able to confirm compliance using one-way SMS.

In an embodiment, if a member selects a two-way SMS service type, the member may receive messages from the health manager regarding the patient's health regimen. In addition, the member may be able to respond to messages, via SMS or the like. As such, the member may provide information to the health manager, such as health-related measurements and/or statistics. The member may also be able to send messages to the health manger to confirm compliance or the like.

In an embodiment, if a member selects a client application service type, a health manager client software application may be installed on a member's mobile device. The health manager client application may receive one or more instructions via general packet radio service ("GPRS") data packet exchanges, a binary SMS message and/or the like. These instructions may be received automatically or manually. In an embodiment, the health manager may be utilized reactively or proactively. FIG. 1 illustrates an exemplary flow chart depicting reactive 100 and proactive 105 utilizations according to an embodiment.

In an embodiment, a reactive utilization 100 may indicate that a member performs an action in response to a trigger from the member's mobile device. For example, a patient's mobile device may display 110 an alert when the patient is scheduled to take a medication. This alert may trigger the patient to perform an action, such as taking 115 a scheduled medication and confirming 120 compliance. In an embodiment, a reactive utilization may be used in conjunction with a one-way SMS service type, a two-way SMS service type and/or a health manager client application service type.

In an embodiment, a proactive utilization 105 may mean that an action is initiated by a member. For example, a member may access 125 the health manager client application on the member's mobile device. The member may select 130 a medication, take 135 the medication and confirm 140 compliance. In an embodiment, a proactive utilization may be used in conjunction with a health manager client application service type. In an embodiment, the reactive and/or proactive utilizations may be repeated 145 for any additional medications.

Figure 2:
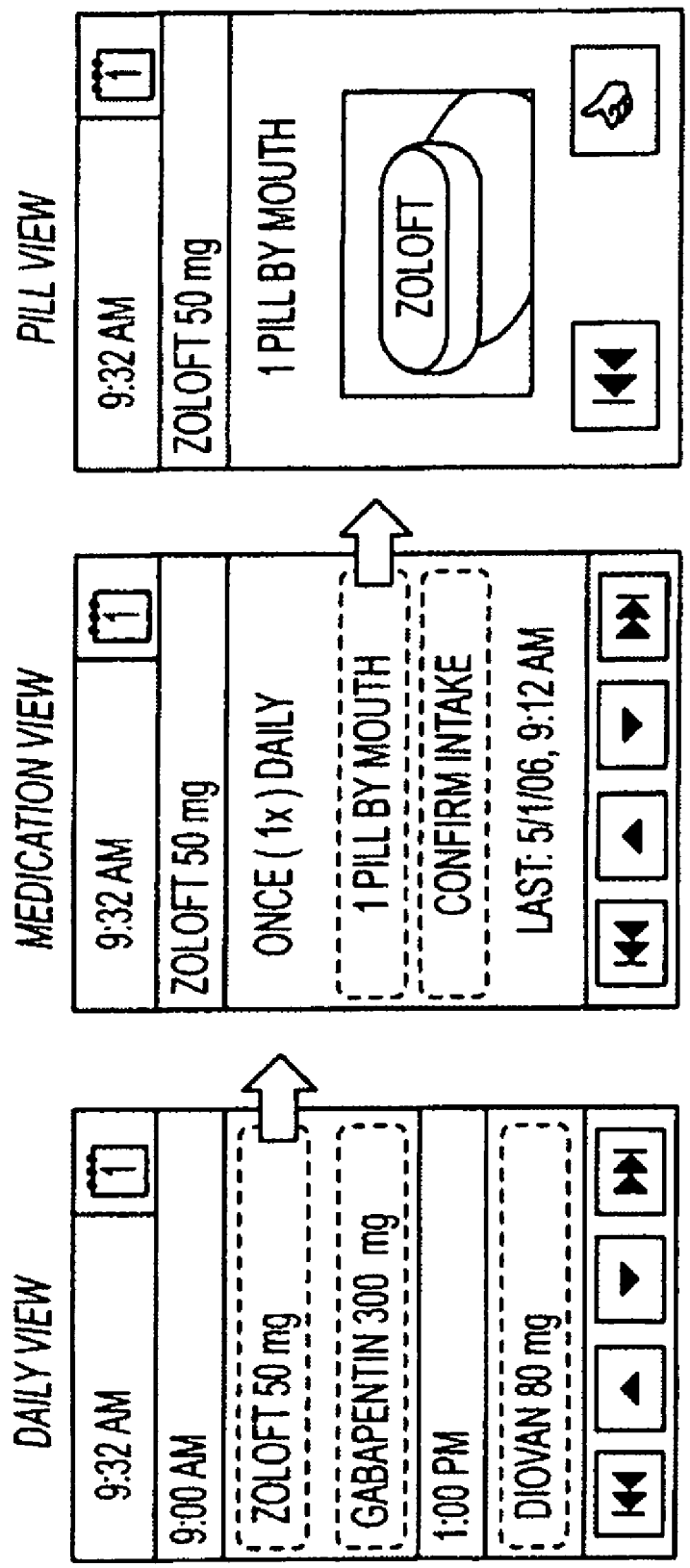
FIG. 2A illustrates an exemplary user interface depicting a medication schedule on a certain day according to an embodiment.
FIG. 2B illustrates an exemplary user interface depicting medication information according to an embodiment.
FIG. 2C illustrates an exemplary user interface depicting an image of a medication according to an embodiment.

FIGS. 2A-2C illustrate exemplary user interfaces associated with the health manager client application that may be accessed via a mobile device or the like. For example, FIG. 2A illustrates an exemplary user interface depicting a medication schedule on a certain day. FIG. 2B illustrates an exemplary user interface depicting medication information according to an embodiment. FIG. 2C illustrates an exemplary user interface depicting an image of a medication according to an embodiment. In an embodiment, the health manager client application may scale the display to fit on the mobile device's display screen. The health manager client application may provide a user the ability to scroll up, down, left, right and the like. In an embodiment, the health manager client application may be launched by selecting an icon located on a display of the mobile device. The health manager client application may be able to access one or more storage mediums associated with the mobile device, such as a database or the like. For example, if a patient confirms intake of a medication, the health manager client application may be able to update a storage medium with this information. Additionally, the health manager client application may be able to search and retrieve information from the storage medium. In an embodiment, the health manager client application may be able to generate alerts. the health manager client application may check for both incoming and outgoing messages.

Figure 21:
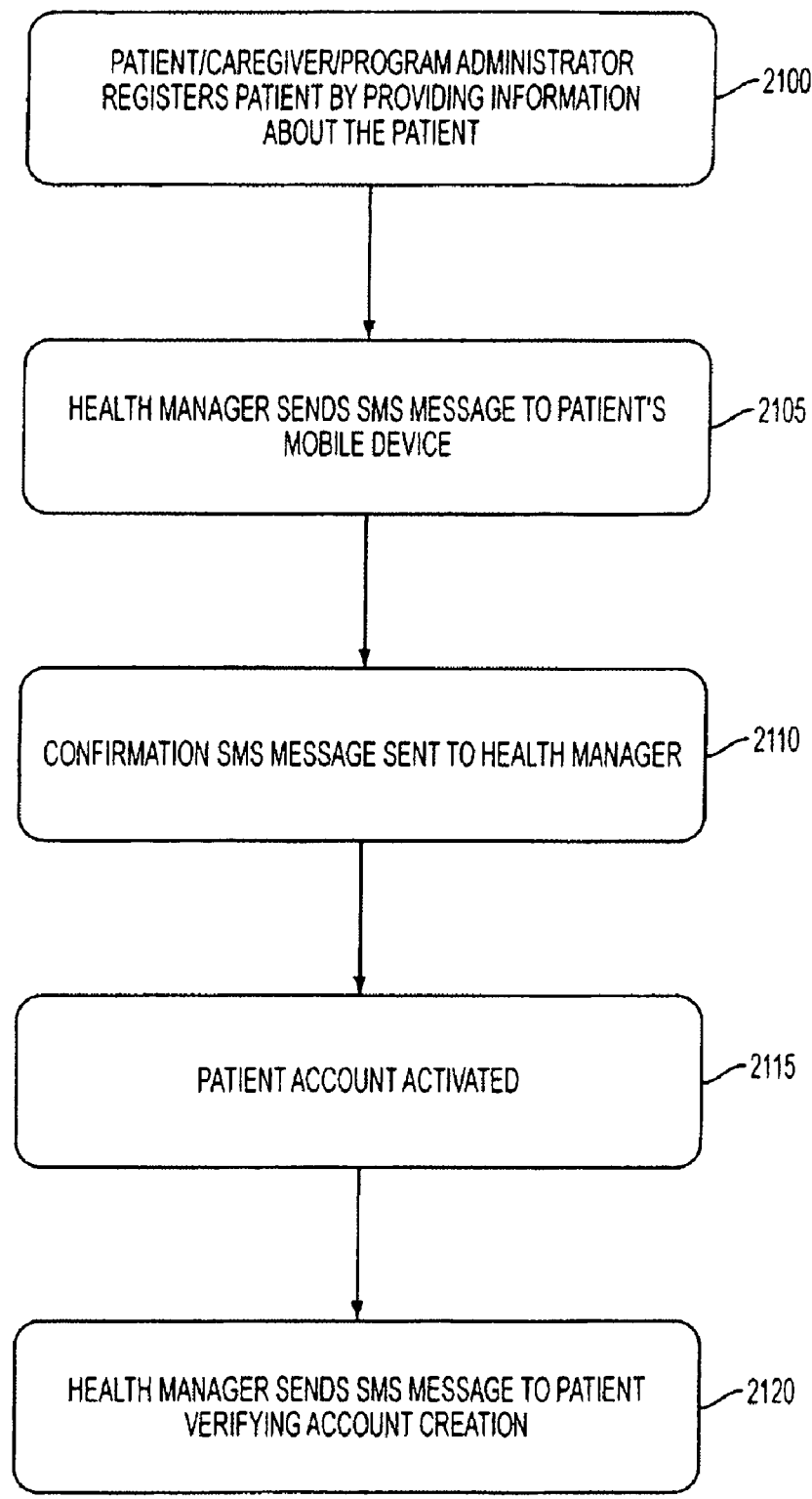
FIG. 21 illustrates a flow chart of an exemplary method of registration according to an embodiment.

In an embodiment, a patient may be registered with a health manager for the provision of health management services. FIG. 21 illustrates a flow chart of an exemplary method of registering according to an embodiment. In an embodiment, the patient may register with the health manager by accessing a website via the Internet to establish a health manager account. In another embodiment, a patient may be registered by another member, such as a physician, a caregiver and/or the like. In an embodiment, a caregiver may be a person other than the patient who has an interest in the patient's health. For example, a caregiver may be a parent, a child, a nurse, or the like.

In an embodiment, information about the patient such as the patient's name, a mobile phone number, a mobile phone carrier, a brand and/or model of the mobile phone, an address, an email address, geographic information, a username, a password and/or the like may be provided 2100. In an embodiment, information associated with one or more caregivers may be provided. This information may include the caregiver's name, a mobile phone number, a mobile phone carrier, a brand and/or model of the mobile phone, an address, an email address, geographic information, a username, a password and/or the like.

In an embodiment, information regarding a health regimen may be provided. A health regimen may be a regulated plan designed to improve the health of a patient. A health regimen may include a plurality of actions the patient is to perform to maintain or improve the patient's health. In an embodiment, a health regimen may include taking one or more medications, such as prescription medication, vitamins, or the like, performing a physical therapy routine or the like. For example, a member may provide information regarding the medications the patient is taking. The information may include the name of the medication, the prescribing physician, dosage information, when the patient is supposed to take the medication, how often the patient is to take the medication and/or the like.

In an embodiment, information regarding the appearance of a medication may be provided. The appearance of a medication may change from refill to refill. This may be because brand name medications may have an different appearance than generic medication. As such, a patient may confirm that the patient is taking the correct medication if the patient can view an image of the medication prior to intake. In addition, a caregiver may be able to access an image of a medication to describe to a patient.

For example, a patient may provide information regarding certain features of a medication such as a form (i.e., pill, liquid, etc.), a color, a size, a shape, an inscription on one or more sides and/or the like. The health manager may use this information to generate an image of the medication. In an embodiment, the medication information and/or the image may be stored on the health manager and/or a storage medium.

In an embodiment, the information provided during registration may be stored in a computer-readable storage medium associated with the health manager, such as a database or the like. In an embodiment, after information associated with the patient is provided 2100, the health manager may send 2105 a message, such as an SMS message, to the patient's mobile device to confirm registration. For example, the message may read, "To confirm account creation, press REPLY, type OK and press SEND." In an embodiment, the patient may send 2110 a message to the health manager to confirm registration, and an account associated with the patient may be activated 2115. In an embodiment, the health manager may send 2120 a message to the patient's mobile device confirming the patient's account was activated. For example, the message may read, "Your account has been created. You can access your account with the username ABC and the password XYZ."

In an embodiment, after registration, a member may access information regarding a health regimen. In an embodiment, a member may access this information by logging on to a health manager by providing a user name, a password, an email address and/or the like. The information may include at least a portion of the regimen for a certain day, a date, an hour, one or more actions associated with the regimen for the day, a time for an action followed by a list of one or more actions to be performed at that time, a confirmation associated with an action, a prescribing physician's name, a prescribing physician's telephone number, a dispensing pharmacy's name, a dispensing pharmacy's telephone number, a dosage, a frequency, one or more special instructions and/or the like. For example, the health manager may generate alerts to remind a patient to take a medication. FIG. 3 illustrates an exemplary form a member may use to identify alerts to be received according to an embodiment.

In an embodiment, a patient may access a medication schedule for a particular day. FIG. 4 illustrates an exemplary medication schedule according to an embodiment. The medication schedule may include one or more intake times 400, one or more corresponding medications 405, dosage information associated with the medications 410, a frequency with which the medications are to be taken (i.e., the days a medication is to be taken, how many times a day a medication is to be taken and/or the like) 415, a prescribing physician's name and telephone number 420, a dispensing pharmacy's name and telephone number 425, an image of a medication 430, a compliance percentage associated with a medication 440, whether a medication has a refill 435 and/or the like.

Figure 5:
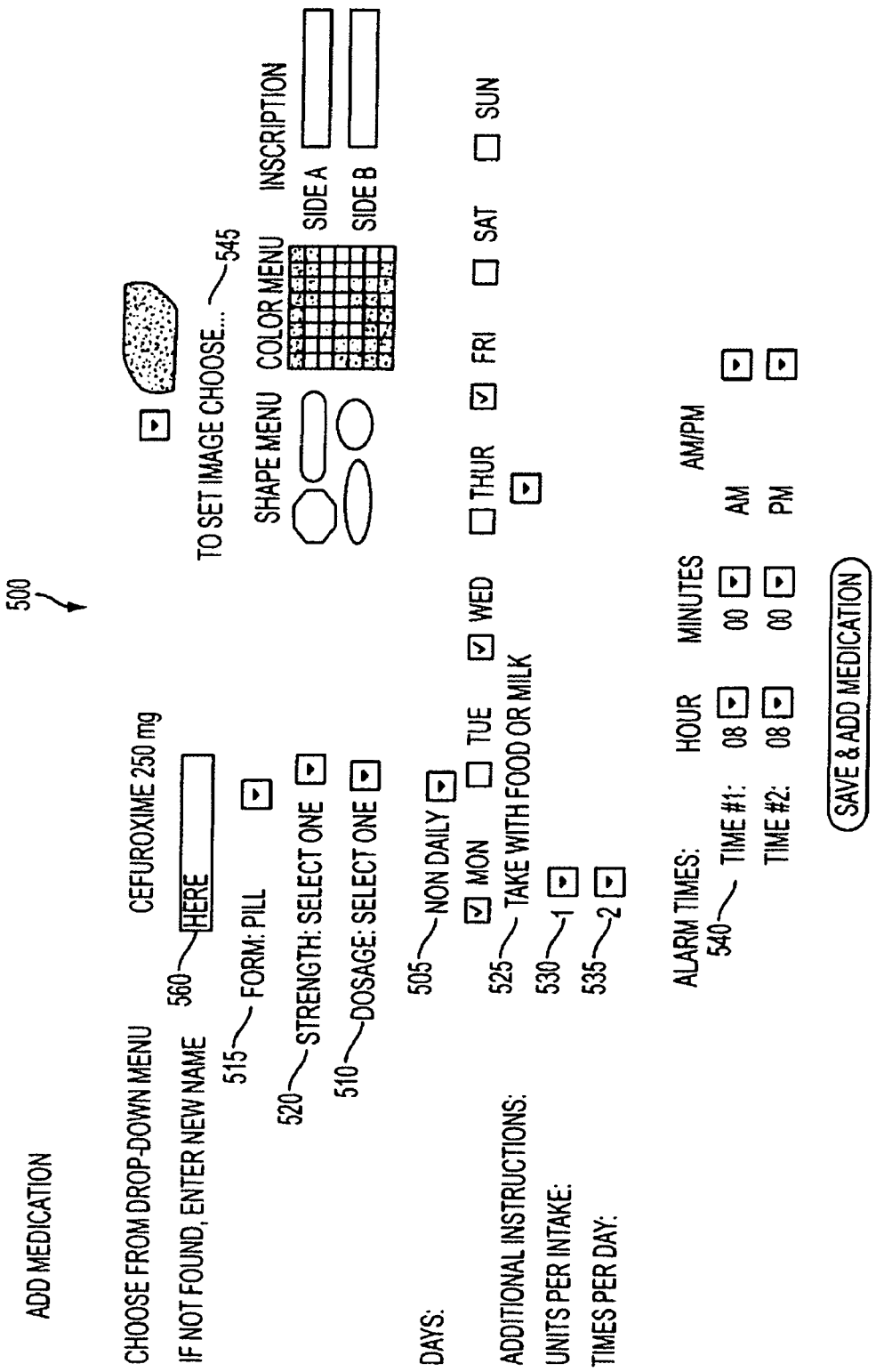
FIG. 5 illustrates a screen shot of an exemplary form that a patient may use to add a medication to a health regimen according to an embodiment.

In an embodiment, a member may add one or more actions to a health regimen, delete one or more actions from a health regimen and/or change one or more actions associated with a health regimen. For example, if a patient is prescribed a new medication, the patient may add information regarding the new medication, such as the medication's name, dosage, frequency and/or the like to a health regimen so the health manager may generate alerts to remind the patient to take the new medication. FIG. 5 illustrates a screen shot of an exemplary form that a patient may use to add a medication to a health regimen. As illustrated by FIG. 5, the patient may be asked to provide information about a new medication such as the medication name 500, 560, the days 505 the patient is to take the medication, the dosage 510 of the medication, the prescribing physician's name and phone number, the dispensing pharmacy's name and phone number, the form of the medication 515, the strength of the medication 520, any additional instructions 525, a unit per intake 530, the number of times the medication is be taken per day 535, alarm times 540, menu(s) for creating a medication image 545 and/or the like. In an embodiment, a patient may select a medication from a dropdown list and/or the like. Medications included in the dropdown list may be medications that have been previously approved and/or verified by a system administrator, a healthcare professional and/or the like. If a medication's name is not contained in the dropdown list, a patient may manually enter the medication's name 560. In an embodiment, information associated with the newly added medication may be verified by a system administrator, healthcare professional and/or the like.

In an embodiment, each newly added medication may be checked against the patient's current medications and/or recent medications for potential drug interactions. Drug interaction information may be stored in a storage medium such as a database or the like. In an embodiment, drug interaction information may be stored in an external third party database. Alternatively, drug interaction information may be stored in a storage medium associated with the health manager. For example, a patient who is currently taking penicillin may be prescribed Diovan. When a member adds Diovan to the patient's health regimen, the health manager may verify that penicillin and Diovan are safe to take together. In an embodiment, if a potentially dangerous interaction is detected, the health manager may send one or more alerts to the patient, a caregiver, a physician and/or the like.

Similarly, the patient may delete one or more actions from a health regimen. For example, if a patient stops taking a medication, the patient may delete the information associated with the medication from the health regimen so the health manager no longer sends the patient alerts to take the medication. In an embodiment, the patient may change information associated with an action of a health regimen. For example, if a physician increases the dosage of a patient's medication, the patient may increase the dosage associated with the medication in the health regimen so the health manager may alert the patient to take the correct dosage.

In an embodiment, a patient may deactivate one or more actions of a health regimen. For example, if a patient temporarily stops taking a medication, the patient may deactivate the medication so the patient does not receive alerts reminding the patient to take the medication. In an embodiment, a patient may later reactivate the action without having to re-enter information about the action. For example, if a patient begins taking a medication that has been deactivated, the patient may simply activate the medication without having to re-enter information regarding the medication such as dosage, form, and/or the like.

In an embodiment, the patient may view a health regimen history. The history may be over a predefined period. For example, a patient may view a 10-day intake history to identify which medications the patient took on a certain day and/or the like. In an embodiment, actions associated with the health regimen that have been performed by the patient may be marked differently than actions that have yet to be performed by the patient and/or actions that were not performed by the patient. For example, if a patient takes the medication and confirms compliance, a first symbol, such as a check mark, a plus sign or other symbol may appear in proximity to the medication for that particular day and time. However, a second symbol may appear in proximity to medications the patient has yet to take. In an embodiment, no symbol may appear in proximity to medications the patient has yet to take. Similarly, a third symbol, such as an 'X' or other symbol, may appear in proximity to medications the patient has missed or failed to take.

In an embodiment, a member having a two-way SMS service type may send a command to a short code to receive information regarding health regimen history. For example, a member may send the command "History" to a predefined short code associated with the health manager. The health manager may send to the member's mobile device at least a portion of the member's history. For example, the health manager may send to the member the last ten intake occasions that were confirmed.

In an embodiment, the information associated with a patient's health regimen may be used to generate one or more alerts. For example, one or more alerts may be sent to the patient's mobile device to remind the patient to perform an action associated with a submitted health regimen. In an embodiment, if a member's service level is a health manager client application, the member's mobile device may generate and display one or more alerts.

In an embodiment, an alert may be a text message, such as a binary SMS message, an email, a multimedia message, such as an MMS message, an automated phone call or the like. In an embodiment, an alert may be sent to a member via secure SMS. A member may install a software application on a corresponding mobile device that facilitates the secure transfer of information, such as that contained in an alert. In an embodiment, the software application may be a Java application. If secure SMS is utilized, a user may be required to provide a unique identifier such as a user name, a password, a passcode and/or the like. This feature may be useful for patients concerned with maintaining privacy and ensuring that third parties are unable to view their medication history.

The alert may include information regarding a patient's health regimen. For example, an alert to remind a patient to take a certain medication may include one or more of the medication's name, the strength of the medication, the units of measure associated with the medication, the dosage, the form of the medication (i.e., pill, liquid, etc.), one or more instructions regarding how to administer the medication, one or more instructions regarding how to respond to the alert, an image of the medication, an embedded link to an image of the medication, the name of the prescribing physician, the phone number of the prescribing physician, the name of the dispensing pharmacy, the phone number of the dispensing pharmacy and/or the like.

As another example, a patient may receive an alert reminding the patient to refill one or more medications. A refill reminder may be received a predefined period of time in advance of the exhaustion of a medication supply. FIG. 6 illustrates an exemplary form a member may complete on the health manager to receive a refill reminder for a medication according to an embodiment. As illustrated by FIG. 6, the member may identify whether the patient wants to receive a refill alert 600, the number of units per container 601, how may days in advance a reminder is to be sent 602, whether the refill is to automatically be sent to a pharmacy 603, a dispensing pharmacy 604, a zip code 605 associated with the dispensing pharmacy, whether the member wants to receive an SMS message when the prescription is filled 606, and/or the like. In an embodiment, the member may select a button, key and/or the like 607 to save the settings.

In an embodiment, the refill reminder may include one or more of a medication name, a dosage, a prescribing physician, a dispensing pharmacy and a phone number of the dispensing pharmacy. In an embodiment, a refill reminder may be sent directly to a pharmacy. A patient may be notified via an email, a text message, a multimedia message, an automated phone call and/or the like when the refill is ready to be picked up or delivered.

In an embodiment, an alert may have a corresponding start date and end date. The start date may be a date that the first alert is to be sent to a patient. The end date may be a date that the last alert is to be sent to a patient. In an embodiment, an alert may be sent one or more times between the start date and the end date.

Figure 7:
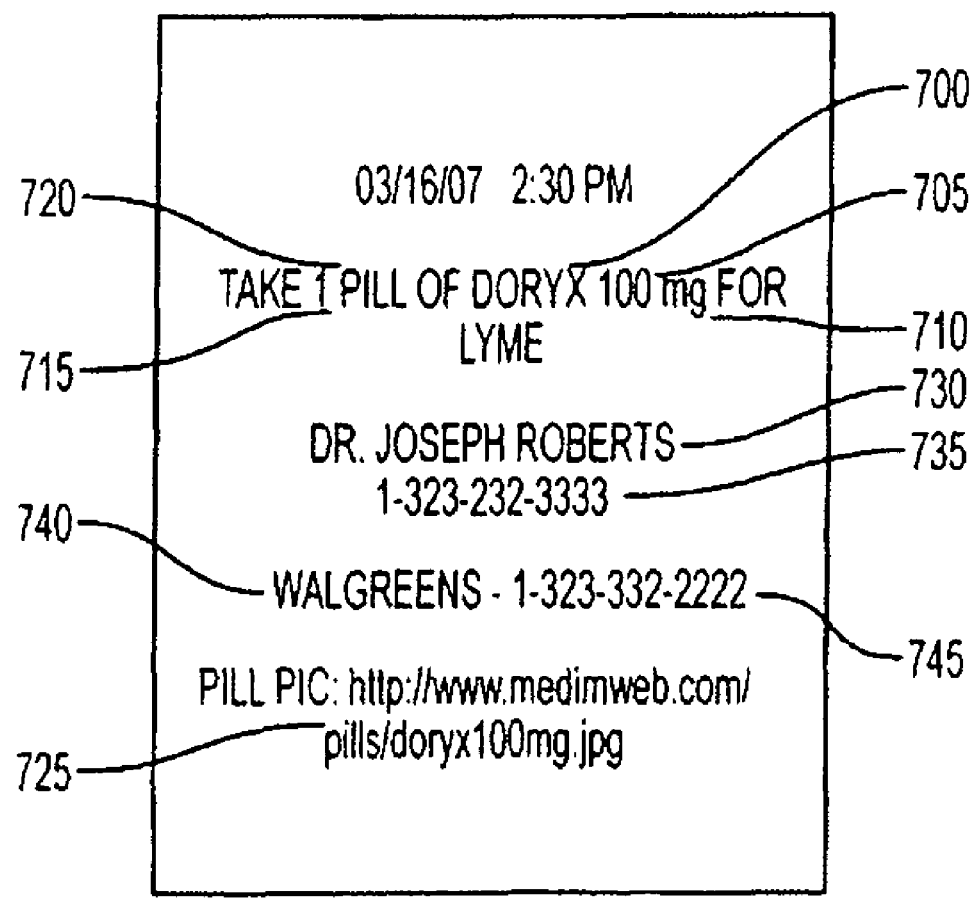
FIG. 7 illustrates an exemplary alert that a patient may receive on a mobile device according to an embodiment.

In an embodiment, an alert may trigger a mobile device to audibly, visually and/or tacitly alert a patient to perform an action associated with a health regimen. For example, a patient may receive an alert reminding the patient to take a medication. FIG. 7 illustrates an exemplary alert that a patient may receive on a mobile device. As illustrated by FIG. 7, the alert may include the medication's name 700, the strength of the medication 705, the units of measure associated with the medication 710, the dosage 715, the form of the medication (i.e., pill, liquid, etc.) 720, one or more instructions regarding how to administer the medication, one or more instructions regarding how to respond to the alert, an image of the medication, an embedded link to an image of the medication 725, the name of the prescribing physician 730, the phone number of the prescribing physician 735, the name of the dispensing pharmacy 740, the phone number of the dispensing pharmacy 745 and/or the like. In an embodiment, the alert may include an advertisement and/or a link to an advertisement.

In an embodiment, the patient may change an alert time associated with one or more actions of the health regimen. FIG. 8 illustrates a screen shot of an exemplary form that a member may use to edit one or more medications. As illustrated, the member may change the information associated with one or more medications, such as the medication name, intake days 800, the frequency per day 805, the units per intake 810, one or more alarm times 815, whether the medication has a refill alert 820, the number of units per container 825, the number of notice for a refill 830, a prescribing physician's name 835 and phone number 840, a dispensing pharmacy's name 845 and phone number 850 and/or the like. In an embodiment, a member may also edit the form of the medication, the strength of the medication, the dosage, the additional instructions, a pill image and/or the like.

In an embodiment, an alert may trigger the mobile device to sound one or more of an audible alarm, a visual alarm and a tactile alarm for a specified period of time, such as ten minutes. In an embodiment, a visual alarm may include a flashing light, LED, or the like. In an embodiment, a tactile alarm may include one or more vibrations or the like. In an embodiment, when an alert is received by a mobile device, information associated with the action to be performed by the patient may be displayed to the patient. For example, an alert may be received by a patient's mobile device reminding the patient to take a medication. One or more of the medication's name, the strength of the medication, the units of measure associated with the medication, the form of the medication (i.e., pill, liquid, etc.), an embedded link to an image of the medication and the like may be displayed to the patient on a display screen of the mobile device.

In an embodiment, the health manager may receive confirmation that the patient has performed the action corresponding to the alert. For example, a patient may provide a compliance code. A compliance code may be one or more alphanumerical characters or other symbols. The patient may provide a compliance code by pressing or otherwise selecting one or more buttons, keys, or the like on the patient's mobile device, computing device and/or other similar device to confirm that the patient has complied with the alert. In an embodiment, the compliance code may be stored on a storage medium associated with the health manager.

In an embodiment, if the patient is associated with a two-way SMS service type or a health manager client application service type, the mobile device may transmit an indication of compliance, such as the compliance code, to the health manager via SMS or the like. Once an indication of compliance has been received, the alert and/or the alarm may be disabled. In an embodiment, the alert and/or the alarm may be disabled by one or more of the health manager, the patient or a caregiver.

For example, a patient who has a two-way SMS service level may receive an alert on a mobile device reminding the patient to take a medication. The alert may specify which medication to take, the dosage of the medication, a picture of the medication and/or any other instructions associated the medication. The patient may confirm compliance with the alert by pressing the 'Reply' button on the mobile device, entering a confirmation code and pressing the 'Send' button on the mobile device to indicate that the patient has taken the medication. In an embodiment, the alert may comprise one or more instructions of how to confirm intake. For example, the alert may include the phrase "To confirm intake, press REPLY, type number 3, and press SEND."

In an embodiment, each medication that a patient is taking may correspond to a unique code, such as a number, a letter, a symbol and/or the like. The patient may confirm compliance by providing the code associated with the medication the patient is to take. For example, a patient may be taking three medications, Advil, penicillin and Vitamin E. Advil may be associated with the code '1', penicillin may be associated with the code '2' and Vitamin E may be associated the code '3.' As penicillin corresponds to '2' in this example, an alert reminding the patient to take penicillin may include an instruction such as, "To confirm intake, press REPLY, type number 2, and press SEND" according to an embodiment.

In an embodiment, a patient having a client application service level or a two-way SMS service level may be requested to provide information regarding an aspect of the patient's health to confirm compliance with an alert. For example, a patient may be asked to provide a measurement of blood sugar to assist the health manager in monitoring the patient's diabetes. Although the example is directed to measuring glucose levels, it is understood that other health-related measurements, including, but not limited to blood pressure, insulin, temperature, weight and the like are covered by the present disclosure.

Figure 9:
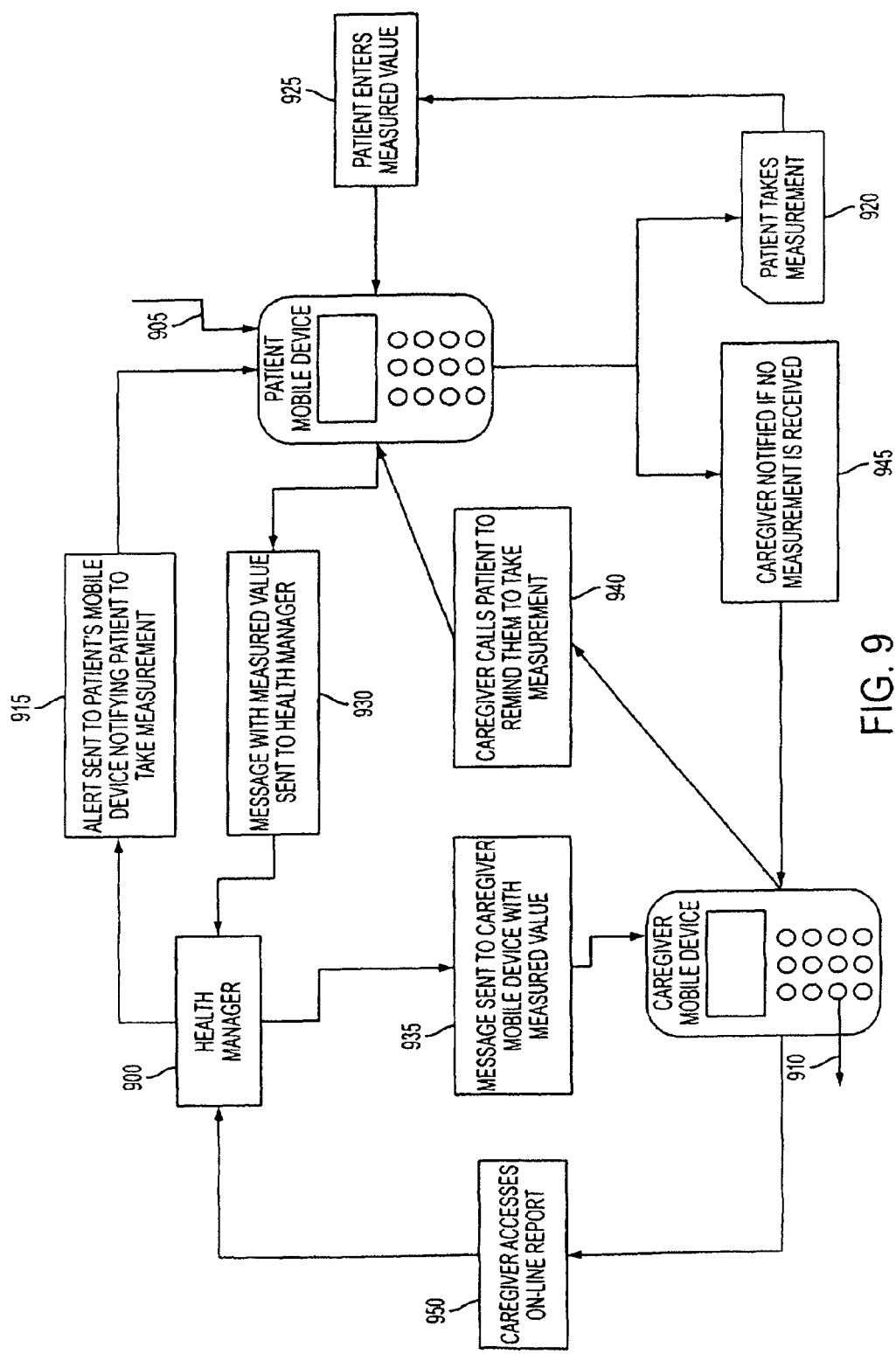
FIG. 9 illustrates an exemplary flow chart of a method of monitoring a patient's compliance with an alert according to an embodiment.

FIG. 9 illustrates an exemplary flow chart of a method of monitoring a patient's compliance with an alert according to an embodiment. As illustrated by FIG. 9, an alert may be received 915 by a patient's mobile device 905 notifying the patient to take a health related measurement, such as measuring the patient's blood sugar level. For example, a patient may receive an SMS alert that reads, "Test blood sugar." FIG. 10A illustrates an exemplary alert that a patient may receive on a mobile device.

In an embodiment, the patient may take 920 the measurement and may enter 925 the measured value via the patient's mobile device 905. For example, the patient may take 920 a blood sugar reading and may enter 925 the blood sugar value on the mobile device 905. The mobile device 905 may send 930 a message that includes the measured value, such as an SMS message, to the health manager 900 using one or more buttons, keys or the like of the mobile device 905. For example, the patient may press the 'Reply' button on the mobile device 905, enter 925 the measured value on the mobile device 905 and press the 'Send' button to transmit the value to the health manager 900. Additional and/or alternate methodologies may be used to transmit a measured value within the scope of this disclosure. The measured value may be stored in a database or other storage medium associated with the health manager 900.

In an embodiment, measured value may be verified by the health manager 900. For example, the health manager 900 may receive a message having a measured glucose level and may determine whether the measured value is within a predefined range. In an embodiment, the range may be specified by one or more of the patient, a physician and a caregiver. If the measured value is not within the predefined range, the health manager may send 935 one or more emergency messages to the patient's mobile device 905 and/or one or more caregivers' mobile devices 910 notifying the patient and the caregivers that the measured value is outside of the predefined range. FIG. 10B illustrates an exemplary alert that may be sent according to an embodiment.

In an embodiment, if the measured value is within the predefined range, the health manager may send 935 one or more messages to the patient's mobile device 905 and/or one or more caregivers' mobile devices 910 that includes the measured value. FIG. 10C illustrates an exemplary alert that a patient and/or one or more caregivers may receive on a mobile device according to an embodiment. In response, a caregiver may contact 940 the patient via a phone call, text message, email or the like.

Figure 11:
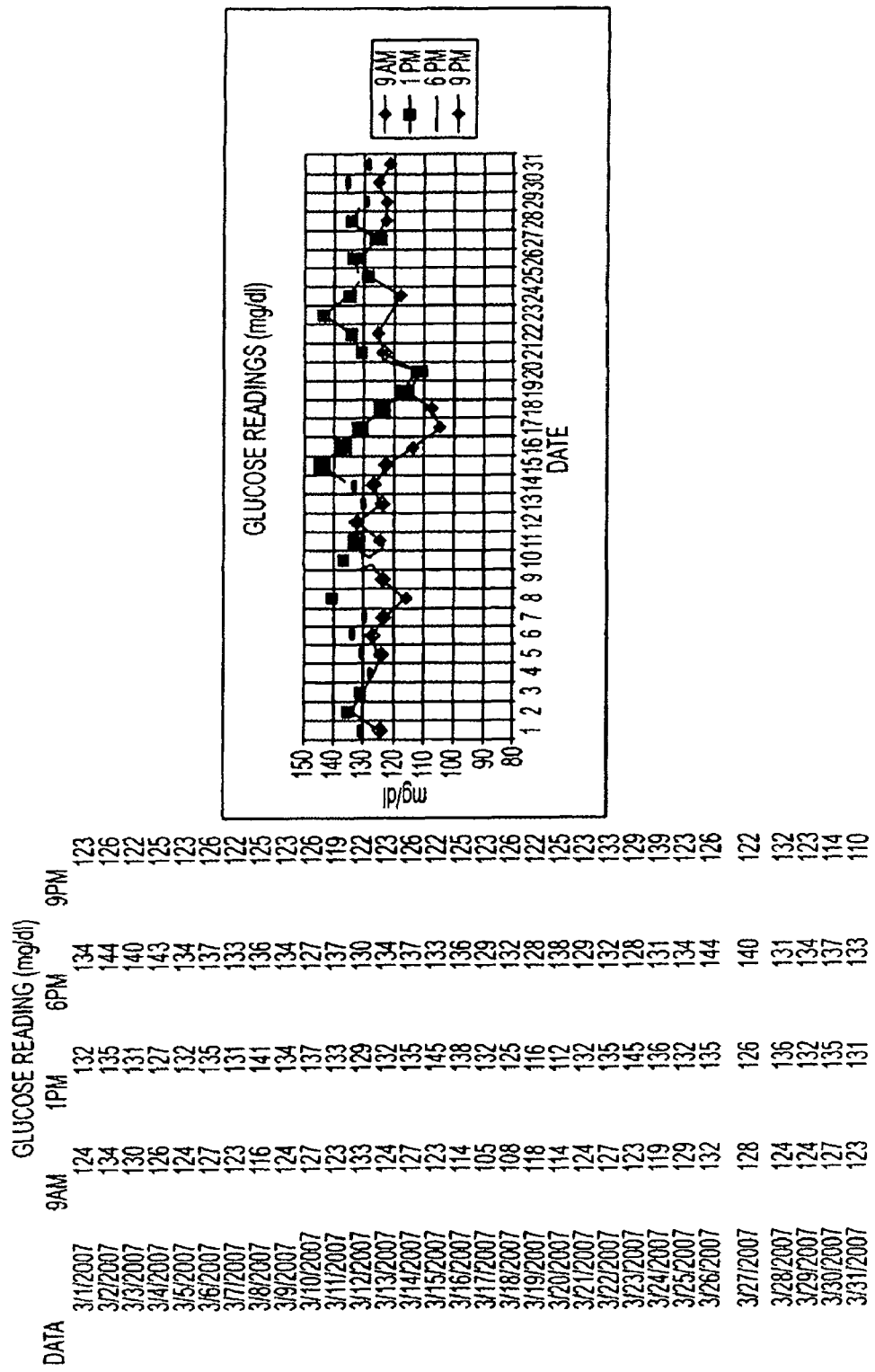
FIG. 11 illustrates an exemplary report according to an embodiment.

In an embodiment, if the health manager does not receive a measured value within a predefined period of time, a caregiver may be notified 945 that a measurement was not received. FIG. 10D illustrates an exemplary message that a caregiver may receive according to an embodiment. In an embodiment, a caregiver may access 950 one or more online reports corresponding to the patient's measurements. The report may be accessed via SMS or from an Internet-enabled device such as a personal computer, a web-enabled phone and/or the like. In an embodiment, the report may include information regarding the measured values over a predefined period of time, a graph, a chart and/or the like. FIG. 11 illustrates an exemplary report according to an embodiment.

In an embodiment, the health manager may receive an indication of compliance from a patient and may store the indication in a database and/or a computer-readable storage medium. In an embodiment, the health manager may send a message to the patient informing the patient that the confirmation has been registered. For example, 81 mg of Aspirin may correspond to code '3' for a certain patient. The patient may receive an alert that reads "Take 1 pill Aspirin 81 mg at 9:00 AM. To confirm intake, press REPLY, type number 3, and press SEND." Upon receiving an indication of compliance, such as an SMS message comprising the number '3', the health manager may register compliance and send a message to the patient such as "Thank you. Your intake of Aspirin 81 mg at 9:00 AM has been registered."

In an embodiment, if the patient responds to an alert with an invalid response, the health manager may send a message to the patient informing the patient that the patient's response was not recognized and to prompt the patient to try again.

In an embodiment, a patient may receive a plurality of alerts on the patient's mobile device at substantially the same time. For example, if a patient is to take two medications at 3 PM, the mobile device may receive two alerts, where each alert corresponds to a medication. Once the patient has taken the medication that is the subject of the first alert, the patient may press or otherwise select a key or button on the mobile device to indicate compliance. In an embodiment, an audible alarm may continue to sound and information associated with the second medication may be displayed to the patient. This procedure may be repeated for any number of alerts.

In an embodiment, a patient may perform an action of a health regimen and confirm compliance prior to receiving an alert. For example, a patient may be scheduled to take medication at 2:15 PM on a certain day. The patient may have a meeting starting at 2 PM that the patient does not want to be interrupted by a reminder to take medication. As such, the patient may take a medication prior to 2:15 PM, confirm compliance and thus disable the alert. For example, a patient having a health manager client service type may be able to logon to the health manager client application via a mobile device, select a medication, confirm compliance and thus disable the alert.

In an embodiment, the health manager may notify the patient and/or one or more caregivers if a patient confirms compliance more than an expected number of times over a specified period of time. For example, a patient may be alerted to take medication twice a day; once at 8 AM and once at 5 PM. As such, the health manager may expect to receive two confirmations a day for the patient. If the patient confirms compliance an additional time, for example, at 6 PM, the health manager may send a message to the patient and/or one or more caregivers notifying them that the patient has exceeded a daily dosage. The message may also suggest a physician be called in case of overdose.

The patient may logon to the health manager by providing a user name, a password and/or the like. The patient may be presented with information regarding a health regimen, such as the day, date, hour, medication schedule and/or the like. Referring back to the previous example, the patient may select the medication having an intake time at 2:15 PM. The health manager may display certain information associated with the medication, such as its name, dosage, frequency, special instructions or the like. The patient may take the medication and may confirm compliance by pressing one or more buttons, keys or the like associated with the mobile device. In an embodiment, because the patient has confirmed compliance prior to the scheduled time of a medication (i.e., 2:15 PM), the alert that was to be sent at that time is disabled.

In an embodiment, one or more people may be notified if the patient fails to respond to an alert after a predetermined period of time. The patient's physician and/or one or more of the identified caregivers may be notified if the patient fails to confirm that the patient took the prescribed medication after a predefined period of time, if the patient's mobile device is turned off when an alert is sent and/or the like. For example, an alert may be sent to a patient to remind the patient to take a medication at 1 PM. If the patient fails to confirm that that patient has taken the medication within a predefined period of time after the alert is received, such as fifteen minutes, then a caregiver may be notified. In an embodiment, a caregiver may be notified by a text message, an email, a phone call and/or the like. In an embodiment, the message that is sent to the caregiver may include the patient's phone number and/or an embedded link to the patient's phone number.

Figure 12:
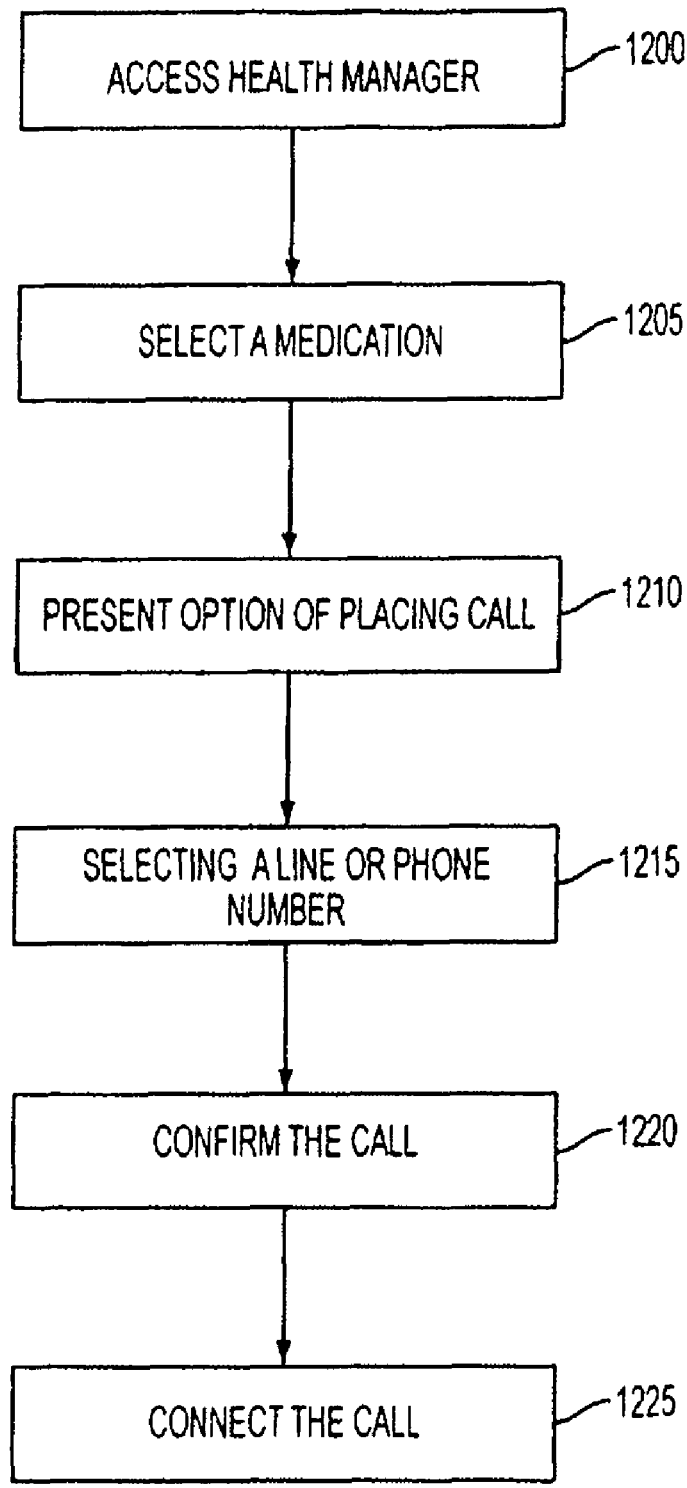
FIG. 12 illustrates a flow chart of an exemplary method of communicating with a person or entity via the health manager according to an embodiment.

In an embodiment, a patient may place a telephone call and/or a voice-over IP call ("VoIP") via the health manager. FIG. 12 illustrates a flow chart of an exemplary method of communicating with a person or entity via the health manager. As illustrated in FIG. 12, a patient may access 1200 the health manager via the health manager client application on a mobile device, a personal computer or other similar computing device. The client may select 1205 a certain medication using one or more buttons, keys, dials, scroll buttons and/or the like on the mobile device, the personal computer or other computing device. The patient may be presented 1210 with the option of calling a physician, calling a pharmacy and/or calling another person or entity. The patient may choose to call a person or an entity by selecting 1215 one or more of a link to a phone number associated with the person or entity, the phone number associated with the person or entity or the like. In an embodiment, the patient may confirm 1220 the call by pressing one or more buttons, keys or the like. Upon confirmation, the call may be connected 1225 to the selected person or entity.

In an embodiment, the patient may access the health manager via a mobile device, and the mobile device may automatically connect the call to the dialed person and/or entity. For example, a patient may receive a refill reminder three days before the patient's medication is exhausted. The refill reminder may include the dispensing pharmacy's phone number and/or a link to the dispensing pharmacy's phone number. The patient may select the link and/or the phone number to initiate a call between the patient's mobile device and the pharmacy. In an embodiment, one or more plug-ins may be required to connect a VoIP call between the patient's personal computer and/or other similar computing device and the dialed number.

In an embodiment, the health manager may determine a compliance percentage for a patient. A compliance percentage may be the ratio of times the patient has confirmed an action to the number of times the patient was supposed to perform the action over a specified time period. For example, if a patient is to take a medication fourteen times per week, but the patient confirms compliance only eight times one week, the patient's compliance percentage for that week is approximately 57% (i.e., 8/14). In an embodiment, the compliance percentage may be stored by the health manager and/or a storage medium associated with the health manager. The health manager may periodically send one or more messages to one or more of the patient and one or more caregivers.

In an embodiment, the message may include a report of the patient's compliance percentage for one or more actions over a certain period of time. FIG. 13 illustrates an exemplary compliance report that may be sent to or accessed by a member. As illustrated by FIG. 13, the report includes the intake times 1300 associated with a medication 1305 for a certain week. The report also includes the number of times the patient confirmed compliance 1310, the number of times the patient was supposed to take the medication 1315 and a compliance percentage 1320. In an embodiment, the health manager may send one or more messages to one or more of the patient and one or more caregivers if a compliance percentage falls below a specified threshold. For example, the health manager may send a message to the patient and the patient's caregiver if the patient's compliance percentage for a specific medication falls below 50%. In an embodiment, a member may identify a specific date range, such as from a calendar menu, from which to view one or more compliance rates.

In an embodiment, a patient may receive one or more motivational messages based on the patient's compliance with a health regimen. In an embodiment, a motivational message may be sent to a patient based on a compliance percentage and/or a range of compliance percentages over a specified period of time. FIG. 14 illustrates an exemplary online form a member may use to create one or more motivational messages. As illustrated by FIG. 14, the member may select a lower threshold 1400 and upper threshold 1405 of a range of compliance, a start date 1410, an end date 1415, a delivery time 1420, a delivery frequency 1425 and/or the like. The member may also enter one or more motivational messages 1430. In an embodiment, the form may also include an area 1435 for a healthcare professional's signature and/or the like. Table 1 illustrates exemplary compliance percentages and corresponding motivational messages that may be sent to a patient on a medication regimen according to an embodiment.

TABLE 1

| Compliance | Motivational Message |
| --- | --- |
| 60-70% | "Your compliance for this week is 63%. Failing to take your medication may cause additional health problems. Let's try to increase compliance for next week." |
| 70-80% | "Your compliance for this week is 77%. This is very good. Let's try to increase compliance to over 80% for next week. This will improve your treatment outcome." |
| 80-90% | "Your compliance for this week is 84%. Good job! Let's try to increase compliance to over 90% for next week. This will improve your treatment outcome." |
| 90-100% | "Your compliance for this week is 97%. Great job! Keep up the good work." |

In an embodiment, the motivational message may be sent to the patient via an email, a text message, a multimedia message, a one-way binary SMS message, a binary SMS message, an automated phone call or the like. The patient may receive the motivational message on a mobile device, a personal computer and/or other similar computing device. In an embodiment, a system administrator, a healthcare provider and/or the like may define one or more of the days, the times, the start date, the end date and/or the content associated with a motivational message.

In an embodiment, the patient may receive one or more rewards based on the patient's compliance over a predefined period of time. For example, if a patient meets or exceeds a specified percentage of compliance for a certain month, the patient may earn a reward. In an embodiment, a minimum compliance level may be determined by a healthcare professional, a program sponsor, such as a pharmaceutical company or a health insurance company or the like. The minimum level of compliance may correspond to a level that is expected to have a positive treatment outcome for a patient. If the patient meets or exceeds this minimum level, the patient may earn a reward. In an embodiment, the type of reward may be based on the patient's compliance percentage. Table 2 illustrates exemplary ranges of compliance percentages and corresponding rewards for a patient being treated with Medication A according to an embodiment.

TABLE 2

| Compliance Percentage (%) | Reward |
| --- | --- |
| 70-80 | 10% off Medication A |
| 80-90 | 15% off Medication A |
| 90-100 | 20% off Medication A |

The reward may include a coupon that is redeemable for a certain amount or percentage off a certain medication, a discount on a co-payment and/or the like. In an embodiment, the reward may be a coupon or other similar discount that may be downloaded to the patient's mobile device for redemption.

In an embodiment, a patient may receive notification of a reward by an email, a text message, a multimedia message, a one-way binary SMS message, a binary SMS message, an automated phone call or the like. In an embodiment, the patient may also access information regarding the patient's rewards by logging on to the health manager. The patient may view one or more reports regarding the patient's reward status which may include a compliance percentage associated with one or more actions, a duration of time, and/or the like. The patient may also be able to view, print and/or email a reward. For example, if the patient earns a reward coupon, the patient may logon to the health manager and print the coupon for redemption.

Figure 15:
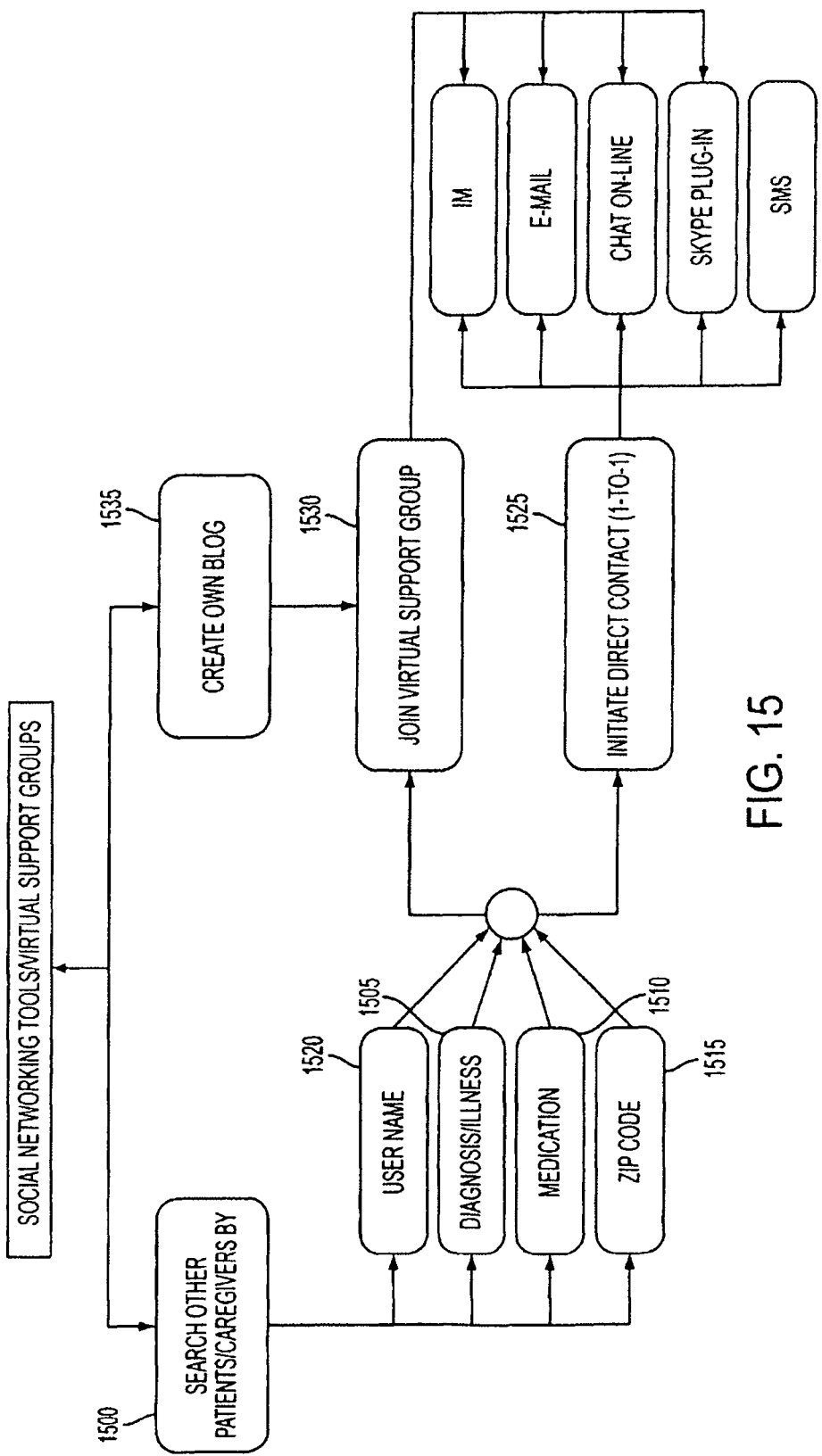
FIG. 15 illustrates a flow chart for an exemplary method of utilizing a social network associated with a health manager according to an embodiment.

In an embodiment, a patient may be able to use the health manager as a social network to locate and communicate with others who utilize the health manager. In an embodiment, the health manager may include a storage medium, such as a database, that comprises information associated with its members. A member may include a patient, a physician, a caregiver and/or the like. FIG. 15 illustrates a flow chart for an exemplary method of utilizing a social network associated with a health manager according to an embodiment. As illustrated by FIG. 15, a member may be able to search 1500 for other members using certain search criteria. For example, a patient may want to locate other patients having the same illness 1505 that they have. Other search criteria may include medication 1510, zip code 1515, name 1520, geography and/or the like. In an embodiment, the patient may be able to identify certain search criteria by entering a natural language query, selecting the criteria from a dropdown menu, selecting a radio button, a checkbox or the like in proximity to the criteria and/or the like. In an embodiment, a member may be able to further limit a query by designating additional criteria. For example, a patient may be able to search for patients having the same illness as they have. The patient may be able to further narrow the search results by searching for members in a certain zip code or within a specified distance from a certain zip code.

In an embodiment, a member may choose to opt in or opt out of the virtual support group. A member who opts out may be removed from the plurality of members who may be searched. As such, even if a member who opts out meets certain search criteria, information concerning that member may not be displayed to others. In an embodiment, if a member opts in, the member may identify information that is permissible to display to others. For example, a member may not want to have the member's name displayed. As such, the member may create an alias or simply be referred to as 'anonymous.'

Information associated with the one or more members who meet the search criteria may be displayed. In an embodiment, a profile associated with each member may be displayed. The profile may include the illness from which the member suffers, how long the member has suffered from the illness, medications the member is taking, the member's zip code, whether the member is open to being contacted by others and the like. In an embodiment, a member may provide information upon registration for the health manager services.

In an embodiment, a member may initiate 1525 contact with one or more members. The member may choose to contact the one or more other members via email, text message, chat, instant messaging, phone call, VoIP call and/or the like. In an embodiment, a member may have an option as to whether other members can contact them. A member may also indicate one or more members by whom they do not want to be contacted.

In an embodiment, a member may be able to join 1530 a virtual support group. A virtual support group may include a plurality of members who share a common characteristic regarding their health. For example, patients having lung cancer and their caregivers may represent a virtual support group according to an embodiment. Members who belong to a virtual support group may contact one or more other members of the group via email, text message, chat, instant messaging, a phone call, a VoIP call and/or the like. Members who belong to a virtual support group may post information in an area, such as a website, a chat room, a bulletin board, and/or the like, that is accessible by other members of the group.

In an embodiment, members of the health manager may be able to create 1535 and post a blog or the like. For example, a patient or a caregiver may create a blog in order to document their illness and their treatment. In an embodiment, the blog may be viewable by other members of the health manager. In an embodiment, the author may be able to limit access to their blog.

In an embodiment, a customizable RSS feed may be included on a member's account page. For example, a patient may logon to a health manager by providing a username, password and/or the like. If the patient suffers from Hepatitis C, an RSS feed may be included on an account page the patient may access after successfully logging onto the health manager. The RSS feed may display relevant information regarding Hepatitis C, such as news headlines, research results and/or the like. In an embodiment, a patient may also receive a link to an RSS feed via SMS to the patient's Internet-enabled mobile device.

Figure 16:
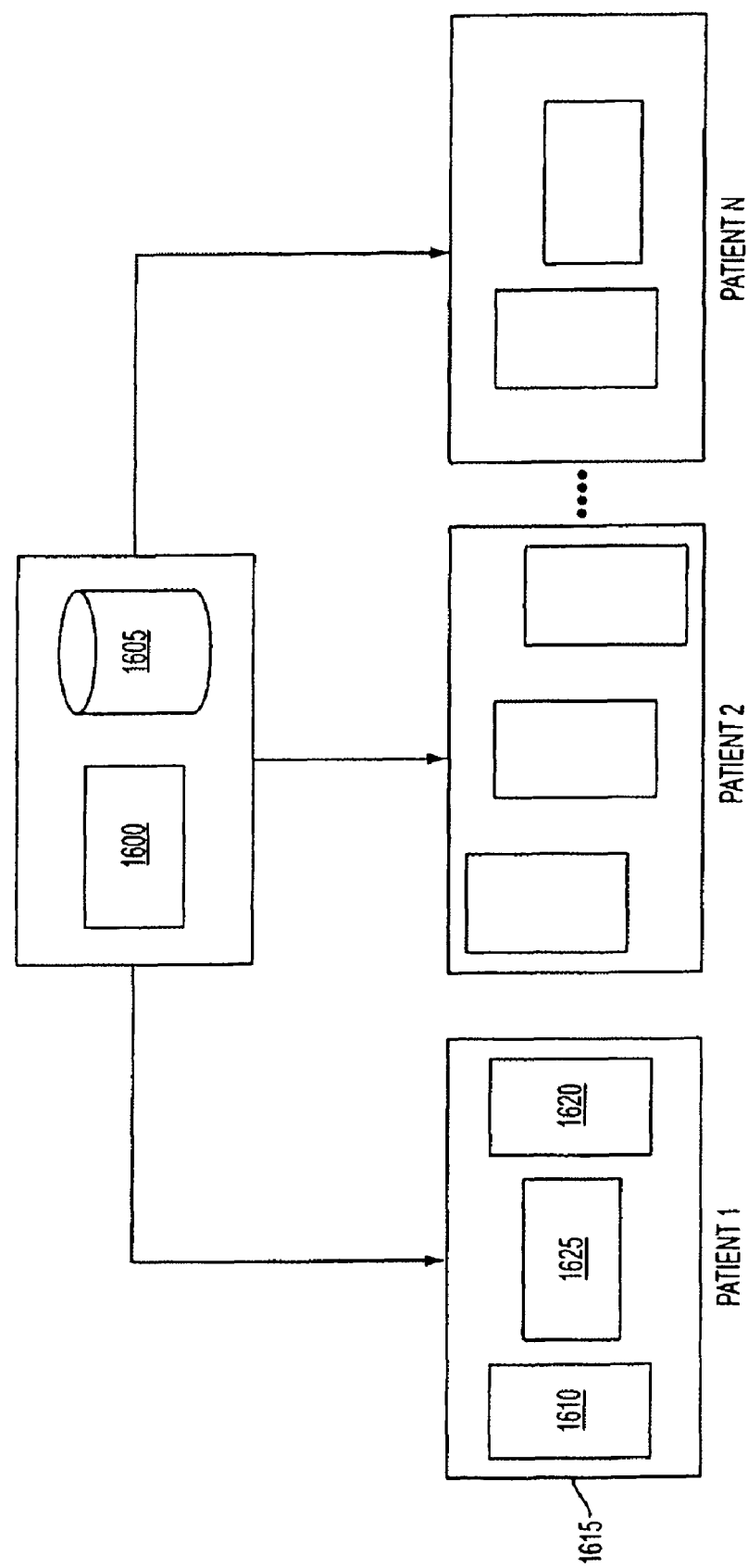
FIG. 16 illustrates an exemplary system for monitoring patient compliance with a health regimen according to an embodiment.

FIG. 16 illustrates an exemplary system for monitoring patient compliance with a health regimen according to an embodiment. The system may include one or more computing devices 1600 in communication with a computer-readable storage medium 1605. In an embodiment, the health manager may be a software application that may be housed on a computing device 1600. Alternatively, the health manager may be a standalone application. The computing device 1600 may be in communication with a plurality of mobile devices, personal computers and/or other computing devices. For example, as illustrated by FIG. 16, the computing device 1600 may be in communication with a mobile device 1610 associated with Patient 1 1615, a mobile device 1620 associated with Patient 1's caregiver, and Patient 1's personal computer 1625.

In an embodiment, a health manager may be used as a medication adherence system for a plurality of patients. For example, a physician who is conducting a clinical trial may utilize a health manager to monitor compliance of a plurality of patients. In an embodiment, a healthcare professional may create one or more programs. Each program may correspond to a health issue, a disease, an illness and/or the like. Each program may comprise one or more patients. FIG. 17 illustrates exemplary information that may be displayed to a healthcare professional regarding a plurality of patients who have had liver transplants.

In an embodiment, one or more administrator settings may be provided for each program. FIG. 18 illustrates an exemplary form a healthcare professional may use to identify one or more administrator settings. As illustrated by FIG. 18, the healthcare professional may provide program information 1800, such as a program name, program manager information 1805 and permission information 1810. In an embodiment, program manager information 1805 may include a program manager's time zone, first name, last name, cellular phone number, cellular carrier, user name, password and/or the like. In an embodiment, permission information 1810 may include information associated with individuals who are granted permission to access information associated with a program. For example, as illustrated in FIG. 18, Joe Smith 1815 may have administrator permissions for the program Hepatitis C, while Mary Jones 1820 may only have view only access. In an embodiment, a healthcare professional may be able to add, delete and/or edit permission information associated with one or more users.

In an embodiment, a healthcare professional may provide information regarding one or more patients in a program. FIG. 19 illustrates an exemplary form a healthcare professional may use to enter such information. The information may include patient account and caregiver information 1900, medication and treatment information 1905, messaging information 1910, a patient activity log 1915, notes 1920 and/or the like. The healthcare professional may also provide information such as the patient's name, time zone, phone number, mobile carrier and/or the like.

In an embodiment, a healthcare provider may add, delete and/or edit information associated with one or more patients. For example, a healthcare provider may add, delete and/or edit medications associated with one or more patients, information associated with a caregiver for one or more patients and/or the like. A healthcare professional may also add and/or delete patients from one or more programs and send motivational messages to one or more patients as discussed above.

In an embodiment, a healthcare professional may monitor compliance of a plurality of patients by using alerts as discussed above. For example, each patient that is participating in a clinical trial of a medication may receive one or more alerts reminding them to take the medication. The healthcare professional may use the health manager to monitor the treatment and compliance of the patient's in the clinical trial as well as monitor and detect patterns or trends in symptoms, treatment and/or the like associated with the patients.

Figure 20:
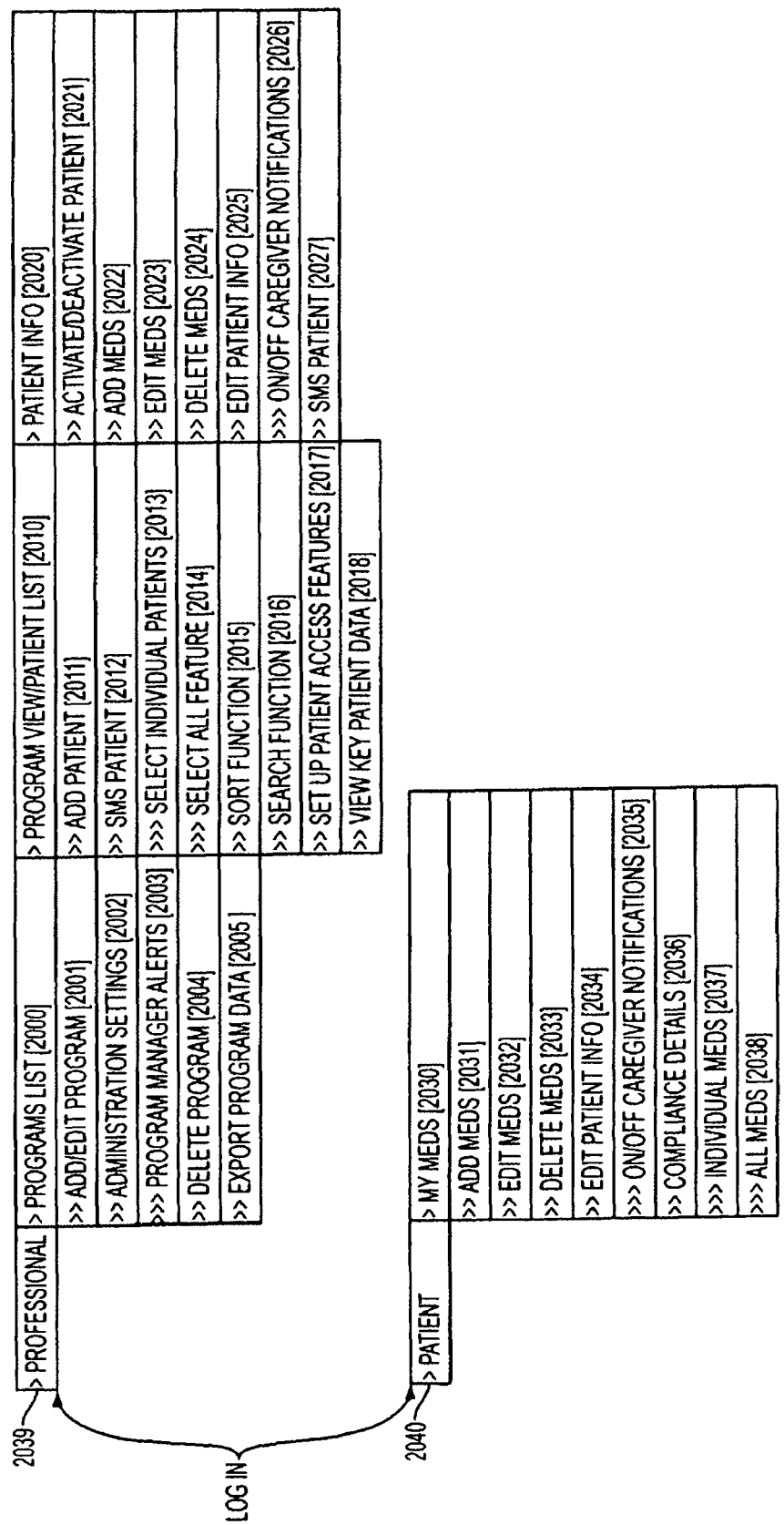
FIG. 20 illustrates a flowchart of exemplary features of a health manager used to manage large patient populations according to an embodiment.

FIG. 20 illustrates a flowchart of exemplary features of a health manager used to manage large patient populations according to an embodiment. As illustrated by FIG. 20, the features may differ depending on whether a patient 2040 or a healthcare professional 2039 is utilizing the health manager. For example, a patient 2040 may be able to access features such as My Meds 2030, Add Meds 2031, Edit Meds 2032, Delete Meds 2033, Edit Patient Info 3024, Caregiver Notifications 2035, Compliance Details 2036, Individual Meds 2037, All Meds 2038 and/or the like. In an embodiment, these features may correspond to web pages, tabs and/or other documents that may be displayed to a member.

In an embodiment, a My Meds feature 2030 may display a welcome, medication regimen information such as name, compliance rate and/or the like, caregiver information and/or the like. In an embodiment, an Add Meds 2031 feature may allow a patient to identify a medication, a daily or non-daily intake regimen, an intake frequency per day, alert days and/or times for a medication, a monthly intake regimen, additional instructions associated with a medication, refill information, a dosage of a medication, refill information and/or the like.

In an embodiment, an Edit Meds 2032 feature may allow a patient to edit the information associated with a medication, such as the information described above with respect to the My Meds 2030 feature. In an embodiment, a patient may not be allowed to edit the medication's name.

In an embodiment, a Delete Meds 2033 feature may allow a patient to delete one or more medications from a health regimen.

In an embodiment, an Edit Patient Info 2034 feature may allow the patient to edit certain patient and/or account information such as a time zone, a name, a cell phone number, a cell phone provider, an email address, a password and/or the like. A patient may also edit information regarding one or more caregivers, such as a caregiver's name, cell phone number, cell phone carrier, alert times and/or the like.

In an embodiment, a Caregiver Notification 2035 feature may allow a patient to activate or deactivate alerts associated with one or more caregivers.

In an embodiment, a Compliance Detail 2036 feature may display compliance information, such as a compliance rate for a certain period of time.

In an embodiment, an Individual Meds 2037 feature may display compliance information associated with a certain medication.

In an embodiment, an All Meds 2038 feature may display compliance information corresponding to every medication associated with a patient.

In an embodiment, a healthcare professional 2039 may be able to access features such as Program List 2000, Add/Edit Program 2001, Administration Settings 2002, Program Manager Alerts 2003, Delete Program 2004, Export Program Data 2005, Program View/Patient List 2010, Add Patient 2011, SMS Patient 2012, Select Individual Patients 2013, Select All 2014, Sort 2015, Search 2016, Set Up Patient Access 2017, View Key Patient Data 2018, Patient Info 2020, Activate/Deactivate Patient 2021, Add Meds 2022, Edit Meds 2023, Delete Meds 2024, Edit Patient Info 2025, Caregiver Notifications 2026, SMS Patient 2027 and/or the like. In an embodiment, these features may correspond to web pages, tabs and/or other documents that may be displayed to a member.

In an embodiment, a Program List 2000 feature may allow a healthcare professional to administrate information such as name, contact information, program names, program manager information, program start dates, program end dates and/or the like.

In an embodiment, an Add/Edit Program 2001 feature may allow a healthcare professional to add and/or edit one or more of a program name, program manager information, dates, access rights and/or the like.

In an embodiment, an Administration Settings 2002 feature may allow a healthcare professional to grant others access rights, manipulate program information and/or the like.

In an embodiment, a Program Manager Alert 2003 feature may allow a healthcare professional to identify one or more levels of compliance associated with one or more patients. In an embodiment, the level of compliance may indicate the level below which the healthcare provider should be notified.

In an embodiment, a Delete Program 2004 feature may allow a healthcare provider to delete one or more programs.

In an embodiment, an Export Program Data 2005 feature may allow a healthcare provider to export program data into a certain format, such as a .cvs format.

In an embodiment, a Program View/Patient List 2010 feature may allow a healthcare provider to access certain information associated with one or more patients such as a program name, a program manager, program manager contact information, a phone number, a patient name, a medication name, a medication compliance rate, an intake regimen, an enrollment date, and account status, an amount of remaining medication and/or the like. The healthcare professional may also send an SMS message to one or more patients, edit program information and/or the like.

In an embodiment, an Add Patient 2011 feature may allow a healthcare provider to add certain information about a patient such as a time zone, a name, a cell phone number, a cell phone provider, an email address, a password, SMS reimbursement options and/or the like. A healthcare provider may also edit information regarding one or more caregivers, such as a caregiver's name, cell phone number, cell phone carrier, alert times and/or the like. In an embodiment, a healthcare provider may agree to certain terms and conditions and/or provide an electronic signature.

In an embodiment, an SMS Patient 2012 feature may allow a healthcare provider to send one or more text messages to one or more patients. In an embodiment, a text message to a plurality of patients may be sent at relatively the same time. In an embodiment, a healthcare provider may identify one or more patients to which a message may be sent.

In an embodiment, an Select Individual Patient 2013 feature may allow a healthcare provider to select an individual patient and/or a group of patients.

In an embodiment, a Select All 2014 feature may allow a healthcare provider to select all patients with a single action, such as a mouse click.

In an embodiment, a Sort 2015 feature may allow a healthcare provider to sort information based on certain criteria, such as name, zip code and/or the like In an embodiment, a Search 2016 feature may allow a healthcare provider to search for certain information within a program and/or the like.

In an embodiment, a Set Up Patient Access 2017 feature may allow a healthcare provider to identify the information a patient may view and/or change.

In an embodiment, a View Key Patient Data 2018 feature may allow a healthcare provider to view certain information associated with one or more patients such as a patient name, a medication, a compliance rate, an intake schedule, an enrollment date, an account status and/or the like.

In an embodiment, a Patient Info 2020 feature may allow a healthcare provider to access certain patient information such as an account status, a patient name, medication and treatment information, a cell phone number, an email address, caregiver information and/or the like. The healthcare provider may also edit medication information and/or delete medication information.

In an embodiment, an Activate/Deactivate Patient 2021 feature may allow a healthcare provider to activate and/or deactivate a patient from participating in a program.

In an embodiment, an Add Medication 2022 feature may allow a healthcare provider to identify a medication, a daily or non-daily intake regimen, an intake frequency per day, alert days and/or times for a medication, a monthly intake regimen, additional instructions associated with a medication, refill information, a dosage of a medication, refill information and/or the like.

In an embodiment, an Edit Medication 2023 feature may allow a healthcare provider to edit information associated with one or more medications. In an embodiment, a healthcare provider may not be allowed to edit a medication's name.

In an embodiment, an Edit Medication 2024 feature may allow a healthcare provider to delete one or more medications and/or the like.

In an embodiment, an Edit Account Settings/Patient Information 2025 feature may allow a healthcare provider to edit information such as a time zone, a name, a cell phone number, a cell phone provider, an email address, a password and/or the like. A patient may also edit information regarding one or more caregivers, such as a caregiver's name, cell phone number, cell phone carrier, alert times and/or the like.

In an embodiment, a Caregiver Notification 2026 feature may allow a healthcare provider to activate and/or deactivate one or more caregiver notifications.

In an embodiment, an SMS Patient 2027 feature may allow a healthcare provider to send one or more text messages to one or more mobile devices associated with one or more patients.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A method of verifying compliance with a health regimen, the method comprising:
sending, by a computing device, a first SMS message to a cellular telephone associated with a patient at an identified time, wherein the first SMS message is configured to instruct the patient to perform an action;
receiving, by the computing device, from the cellular telephone, within a first period of time, a second SMS message comprising a measurement associated with the action; and
if the measurement is not within a range of values, sending, by the computing device, a third SMS message to one or more of the cellular telephone associated with the patient and a cellular telephone associated with a caregiver, wherein the third SMS message is configured to notify one or more of the patient and the caregiver that the measurement is outside of the range.

2. The method of claim 1, wherein the second SMS message comprises one or more of the following:
a glucose level;
a temperature;
a blood pressure; and
a weight.

3. A method of confirming compliance with a medication alert, the method comprising:
sending, by a computing device to a mobile device, an alert to take a medication, wherein the alert is sent at an intake time associated with the medication, wherein the alert comprises a compliance code and one or more confirmation instructions regarding how to confirm compliance using the compliance code,
wherein the alert is configured to:
trigger one or more of an audible alarm, a visual alarm and a tactile alarm on the mobile device, and
cause information associated with the alert to be displayed to a patient on a display screen of the mobile device, wherein the information comprises the compliance code and the confirmation instructions;

receiving, by the computing device, confirmation of compliance provided by the patient via the mobile device; and in response to receiving the confirmation of compliance within a first period of time, sending, by the computing device, one or more instructions to deactivate one or more of the audible alarm, the visual alarm and the tactile alarm of the mobile device.

4. The method of claim 3, further comprising:

sending, by the computing device, a notification to be displayed on the display screen of the mobile device if an actual intake number varies from an expected intake number, wherein the actual intake number represents a number of times the patient has confirmed taking the medication within a second period of time, wherein the expected intake number represents a number of times the patient is directed to take the medication in the second period of time.

5. The method of claim 3, wherein the alert comprises one or more of the following:

an email;
a GPRS data packet;
a text message;
a multimedia message;
a one-way binary SMS message; and
a two-way binary SMS message.

6. The method of claim 3, wherein the alert comprises one or more of the following:

a name of the medication;
a dosage of the medication;
a form of the medication;
an image of the medication;
a link to an image of the medication;
a name of a prescribing physician;
a phone number of the prescribing physician;
a name of a dispensing pharmacy;
a phone number of the dispensing pharmacy; and
an embedded link to one or more of the phone number of the prescribing physician and the phone number of the dispensing pharmacy.

7. A method of verifying compliance with a health regimen, the method comprising:

sending, by a computing device to a cellular telephone at an intake time, a first SMS message reminding a patient to perform an action associated with a health regimen;

receiving, by the computing device, a second SMS message within a first period of time, wherein the second SMS message comprises a measurement provided by the patient; and in response to the measurement being outside of a range of values, sending, by the computing device to the cellular telephone, a third SMS message to be displayed on a display screen of the cellular telephone that alerts the patient that the measurement is outside of the range.

8. The method of claim 7, wherein the first SMS message comprises one or more of the following:

a name of the medication;
a dosage of the medication;
a form of the medication;
an image of the medication;
a link to an image of the medication;
a name of a prescribing physician;
a phone number of the prescribing physician;
a name of a dispensing pharmacy;
a phone number of the dispensing pharmacy; and
an embedded link to one or more of the phone number of the prescribing physician and the phone number of the dispensing pharmacy.

9. The method of claim 1, further comprising:

determining an expected intake number, wherein the expected intake number represents a number of times the patient is directed to take a medication in a second period of time, wherein the second SMS message comprises an actual intake number representing a number of times the patient has confirmed taking the medication in the second period of time.

10. The method of claim 9, wherein sending a third SMS message comprises sending a third SMS message to one or more of the cellular telephone associated with the patient and a cellular telephone associated with a caregiver in response to the actual intake number varying from the expected intake number.

11. The method of claim 1, wherein the first SMS message comprises one or more of the following:

a name of the medication;
a dosage of the medication;
a form of the medication;
an image of the medication;
a link to an image of the medication;
a name of a prescribing physician;
a phone number of the prescribing physician;
a name of a dispensing pharmacy;
a phone number of the dispensing pharmacy; and
an embedded link to one or more of the phone number of the prescribing physician and the phone number of the dispensing pharmacy.

12. The method of claim 1, wherein:

the first SMS message comprises a compliance code and one or more instructions regarding how to confirm compliance using the compliance code; and
the second SMS message comprises the compliance code.

13. The method of claim 12, further comprising, in response to receiving the second SMS message, sending one or more instructions to the cellular telephone to deactivate one or more of an audible alarm, a visual alarm and a tactile alarm of the cellular telephone.

14. The method of claim 7, wherein one or more of the first SMS message and the second SMS message comprise a compliance code.

15. The method of claim 14, further comprising, in response to receiving the second SMS message, sending one or more instructions to the cellular telephone to deactivate one or more of an audible alarm, a visual alarm and a tactile alarm of the cellular telephone.

16. The method of claim 7, wherein the second SMS message comprises one or more of:

a glucose level;
a temperature;
a blood pressure; and
a weight.

* * * * *